United States Patent
Chossat et al.

(10) Patent No.: US 9,953,138 B2
(45) Date of Patent: Apr. 24, 2018

(54) DRUG COMPONENT ADMIXTURE LIBRARY FOR A DRUG INFUSION DELIVERY SYSTEM

(75) Inventors: Olivier Chossat, Les Gras (FR); Timothy Flynn, Duxbury, MA (US)

(73) Assignee: Codman Neuro Sciences Sarl, Le Locle (CH)

( * ) Notice: Subject to any disclaimer, the term of this patent is extended or adjusted under 35 U.S.C. 154(b) by 2015 days.

(21) Appl. No.: 12/803,574

(22) Filed: Jun. 29, 2010

(65) Prior Publication Data
US 2011/0320049 A1    Dec. 29, 2011

(51) Int. Cl.
G06F 19/00    (2011.01)
A61M 5/14    (2006.01)

(52) U.S. Cl.
CPC ........ *G06F 19/326* (2013.01); *G06F 19/3468* (2013.01); *A61M 5/1407* (2013.01)

(58) Field of Classification Search
CPC .... G06F 19/326; G06F 19/3468; A61J 3/002; A61J 2200/70
USPC ....................................... 705/2–3
See application file for complete search history.

(56) References Cited

U.S. PATENT DOCUMENTS

| | | | |
|---|---|---|---|
| 4,193,397 A | 3/1980 | Tucker et al. | |
| 6,269,340 B1 | 7/2001 | Ford et al. | |
| 6,554,822 B1 | 4/2003 | Holschneider et al. | |
| 6,669,683 B2 | 12/2003 | Santini, Jr. et al. | |
| 6,796,956 B2 | 9/2004 | Hartlaub et al. | |
| 6,928,338 B1 | 8/2005 | Buchser et al. | |
| 7,008,413 B2 | 3/2006 | Kovach et al. | |
| 7,347,854 B2 | 3/2008 | Shelton et al. | |
| 7,454,314 B2 | 11/2008 | Holland et al. | |
| 7,471,994 B2 | 12/2008 | Ford et al. | |
| 7,715,919 B2 | 5/2010 | Osorio et al. | |
| 2003/0040486 A1 | 2/2003 | Demopulos et al. | |
| 2006/0100574 A1 | 5/2006 | Isumi et al. | |
| 2006/0204532 A1 | 9/2006 | John | |

(Continued)

FOREIGN PATENT DOCUMENTS

WO    WO 03/082380    10/2003

OTHER PUBLICATIONS

European Search Report of counterpart EP Application No. 11171952.2, dated Apr. 22, 2016 (9 pages).

*Primary Examiner* — Minnah L Seoh
(74) *Attorney, Agent, or Firm* — Cohen & Hildebrand, PLLC

(57) ABSTRACT

Minimizing improper dosage of a drug admixture (including a single primary drug component and at least one second drug component). For each drug component in the drug admixture, receiving a name of the drug component along with its dosage unit, a maximum dose warning level and a maximum concentration warning level. Receiving a concentration for each of the single primary drug component and the at least one secondary drug component; and a dose setting of only the primary drug component. Automatically calculating a dose of each of the at least one secondary drug component. Generating an alert when: (i) the received dose setting of the primary drug component or calculated dose setting of the at least one secondary drug component exceeds the dose warning level; or (ii) the received concentration of the primary drug component or the at least one secondary drug component exceeds the concentration warning level.

23 Claims, 23 Drawing Sheets

(56) References Cited

U.S. PATENT DOCUMENTS

| | | | |
|---|---|---|---|
| 2006/0258985 A1* | 11/2006 | Russell | 604/151 |
| 2006/0259195 A1* | 11/2006 | Eliuk | A61J 1/20 700/245 |
| 2007/0213598 A1 | 9/2007 | Howard et al. | |
| 2007/0272260 A1 | 11/2007 | Nikitin et al. | |
| 2008/0139907 A1 | 6/2008 | Rao et al. | |
| 2009/0043290 A1* | 2/2009 | Villegas et al. | 604/891.1 |
| 2009/0198208 A1* | 8/2009 | Stavsky | A61J 1/2096 604/407 |

* cited by examiner

FIG. 1A
DRG_LIB_SCR

19.Mar.2008　08:54

DRUG LIBRARY

▲

BACLOFEN
CLONIDINE
MORPHINE
SALINE
Add new drug

▼

FIG. 1D
DRG_OPT_SCR

19.Mar.2008　08:54

DRUG LIBRARY
MORPHINE

Dosage unit: mg
Dose warning level: 010.0 mg/day
Conc warning level: 050.0 mg.mL
Comment:
wwwwwwwwwwwwwww
wwwwwwwwwwwwwww
wwwwwwwwwwwwwww

MODIFY　　REMOVE

MORPHINE →
← BACK KEY
YES: UPDATE LIST
MODIFY →

CONFIRMATION (YES/NO) WITH DRUG NAME

NO ↑　　↓ REMOVE

ACCEPT: UPDATE LIST

ACCEPT: UPDATE LIST

CANCEL OR BACK KEY

ADD NEW DRUG...

FIG. 1B
DRG_LIB_WRN_SCR

19.Mar.2008　08:54

WARNING: Refer to pump instructions for use for the list of approved drugs for MedStream.

ACCEPT　　CANCEL

ACCEPT →

FIG. 1C
EDIT_DRG_NM_SCR

19.Mar.2008　08:54

DRUG NAME
_____

| A | B | C | D | E | F | G | H | I | J |
|---|---|---|---|---|---|---|---|---|---|
| K | L | M | N | O | P | Q | R | S | T |
| U | V | W | X | Y | Z | 0 | 1 | 2 | 3 |
| 4 | 5 | 6 | 7 | 8 | 9 | . | - | % | |
| DEL | | VALIDATION | | | | | | | |

VALIDATION

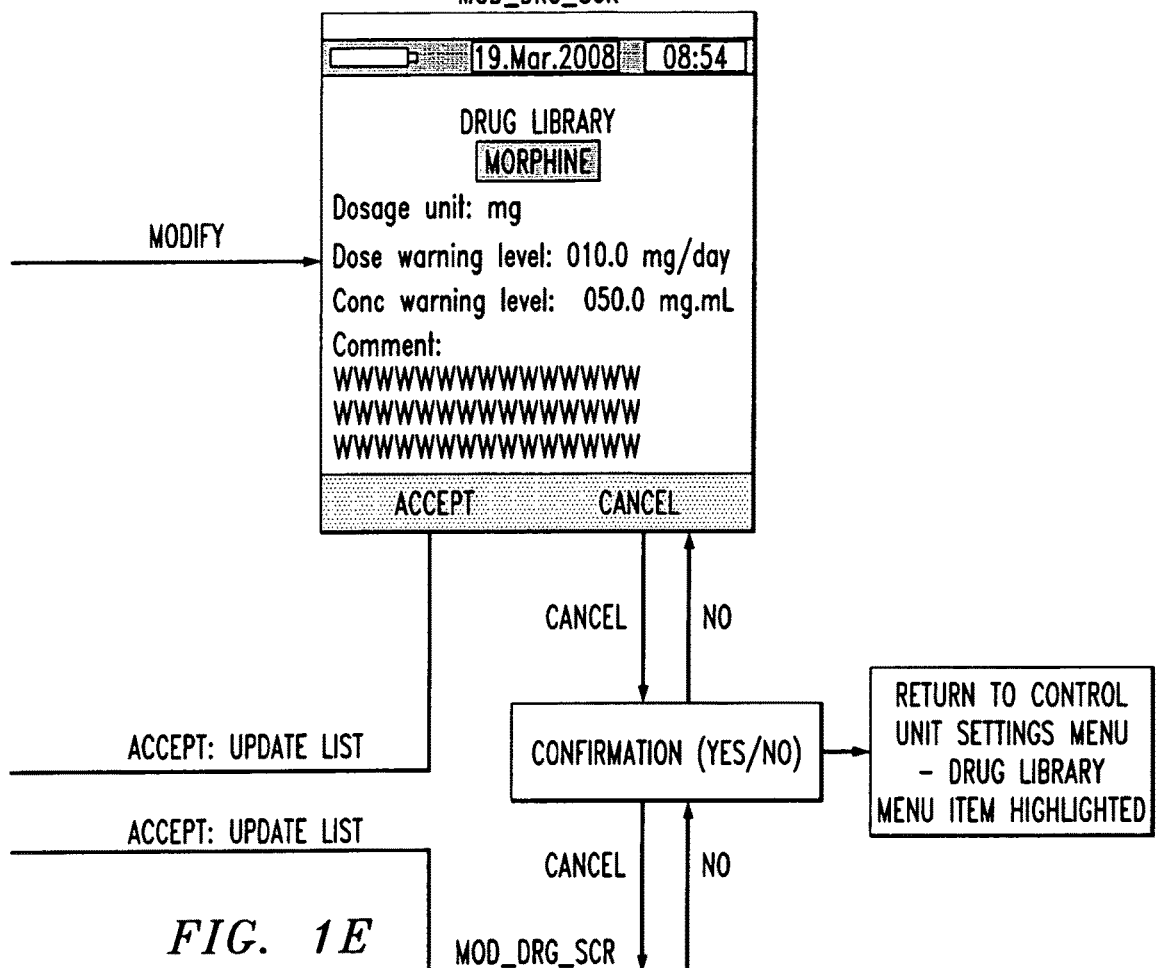
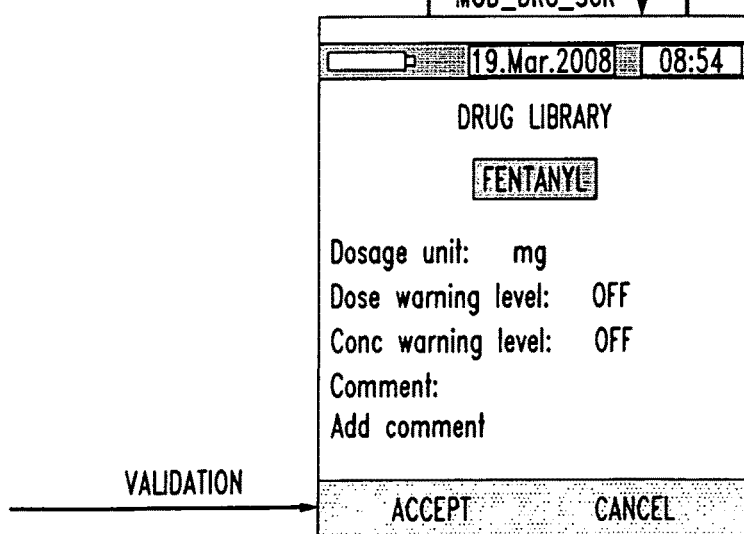

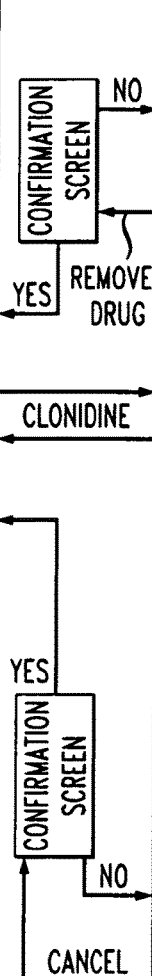

*FIG. 2C*

ACCEPT

| Primary: CLONIDINE  Conc: 10 mg/mL  Daily dose: 2.5 mg | 25.5 ml |
|---|---|

| 19.Mar.2008 | 08:54 |

SET DRUG

| Drug | Conc (/mL) |
|---|---|
| CLONIDINE | 10 mg |
| BACLOFEN | 2000 ug |
| MORPHINE | 25 mg |
| Add drug | |
| | |

Refer to pump instructions for use for the list of approved drugs for MedStream.

| ACCEPT | CANCEL |

*FIG. 2F*

ACCEPT

| Primary: CLONIDINE  Conc: 10 mg/mL  Daily dose: 2.5 mg | 25.5 ml |
|---|---|

| 19.Mar.2008 | 08:54 |

SET DRUG

| Drug | Conc (/mL) |
|---|---|
| CLONIDINE | 25 mg |
| BACLOFEN | 2000 ug |
| Add drug | |
| | |
| | |

Refer to pump instructions for use for the list of approved drugs for MedStream.

| ACCEPT | CANCEL |

FIG. 2G

Primary: CLONIDINE
Conc: 10 mg/mL
Daily dose: 2.5 mg
25.5 ml
19.Mar.2008  08:54

SET DRUG
Change CLONIDINE to
▲
SALINE
MORPHINE
BACLOFEN
CLONIDINE
Add new drug
▼

CHANGE DRUG
BACK KEY

MORPHINE → ENTER DRUG CONCENTRATION
SEE CONTROL UNIT SETTINGS – DRUG LIBRARY
ACCEPT

SET AS PRIMARY (EXAMPLE WITH BACLOFEN)

FIG. 2H

Primary: CLONIDINE
Conc: 10 mg/mL
Daily dose: 2.5 mg
25.5 ml
19.Mar.2008  08:54

SET DRUG

| Drug | Conc (/mL) |
|---|---|
| BACLOFEN | 2000 ug |
| CLONIDINE | 10 mg |
| Add drug | |
| | |
| | |

Refer to pump instructions for use for the list of approved drugs for MedStream.

ACCEPT     CANCEL

FIG. 2I

Primary: CLONIDINE
Conc: 10 mg/mL
Daily dose: 2.5 mg
25.5 ml
19.Mar.2008  08:54

SET DRUG

| Drug | Conc (/mL) |
|---|---|
| MORPHINE | 25 mg |
| BACLOFEN | 2000 ug |
| Add drug | |
| | |
| | |

Refer to pump instructions for use for the list of approved drugs for MedStream.

ACCEPT     CANCEL

ACCEPT ↓    ↑ BACK

FIG. 2J

Primary: CLONIDINE
Conc: 10 mg/mL
Daily dose: 2.5 mg
25.5 ml
19.Mar.2008  08:54

| Old drug | Conc (/mL) |
|---|---|
| CLONIDINE | 10 mg |
| BACLOFEN | 2000 ug |
| | |
| | |

| New drug | Conc (/mL) |
|---|---|
| MORPHINE | 25 mg |
| BACLOFEN | 2000 ug |
| | |
| | |

SAVE DRUG     BACK

FIG. 3A

Primary: MORPHINE
Conc: 25 mg/mL
Daily dose: 10 mg

19.Mar.2008  08:54  25.5 ml

Add Time Block

| Drug | Dose/day | |
|---|---|---|
| MORPHINE | 0 mg | |
| BACLOFEN | 0 ug | |

SAVE PROGRAM    CANCEL

FIG. 3B

Primary: MORPHINE
Conc: 25 mg/mL
Daily dose: 10 mg

19.Mar.2008  08:54  25.5 ml

Ending hour 8H

CANCEL

FIG. 3C

Primary: MORPHINE
Conc: 25 mg/mL
Daily dose: 10 mg

19.Mar.2008  08:54  25.5 ml

PROGRAM SETTING
<Time Block 1> 12AM–8AM
MORPHINE
0.1 < Dose/hour < 4.16 mg
0.8 < Block Dose < 33.28 mg

| DRUG | DOSE/HOUR | BLOCK DOSE |
|---|---|---|
| MORPHINE | 00250 mg | 020.00 mg |
| BACLOFEN | 200 ug | 1600 ug |

ACCEPT    CANCEL

---

Flow: FIG. 3A —ADD BLOCK 1→ FIG. 3B —ENDING HOUR SET→ FIG. 3C —ACCEPT→

BACK KEY returns FIG. 3C → FIG. 3B → FIG. 3A

CANCEL → CONFIRMATION SCREEN TO CANCEL PROFILE EDITION

FIG. 3D

SEL KEY: EDIT BLOCK 2
SCROLL UP: DISPLAY BLOCK 1 INFO
SCROLL DOWN: HIGHLIGHT CANCEL

Primary: MORPHINE
Conc: 25 mg/mL
Daily dose: 10 mg 25.5 ml

19.Mar.2008   08:54

Next Refill: 09.08.2008

< Add Time Block 2 >

| Drug | Dose/day | |
|------|----------|---|
| MORPHINE | 20 mg | |
| BACLOFEN | 1600 ug | |
| | | |
| | | |

| SAVE PROGRAM | CANCEL |

FIG. 3E

Primary: MORPHINE
Conc: 25 mg/mL
Daily dose: 10 mg 25.5 ml

19.Mar.2008   08:54

Next refill: 09.08.2008

< Time Block 1 > 0H − 8H

| Drug | Dose/hour | Dose/day |
|------|-----------|----------|
| MORPHINE | 002.50 mg | 20 mg |
| BACLOFEN | 200 ug | 1600 ug |
| | | |
| | | |

| SAVE PROGRAM | CANCEL |

SAVE PROGRAM OPTION ENABLED ONLY WHEN THE 24 HOURS ARE SET

ACCEPT → (to FIG. 3D)
SCROLL DOWN → (FIG. 3D to 3E)
SCROLL UP → (FIG. 3E to 3D)
SAVE PROGRAM
NO
NO

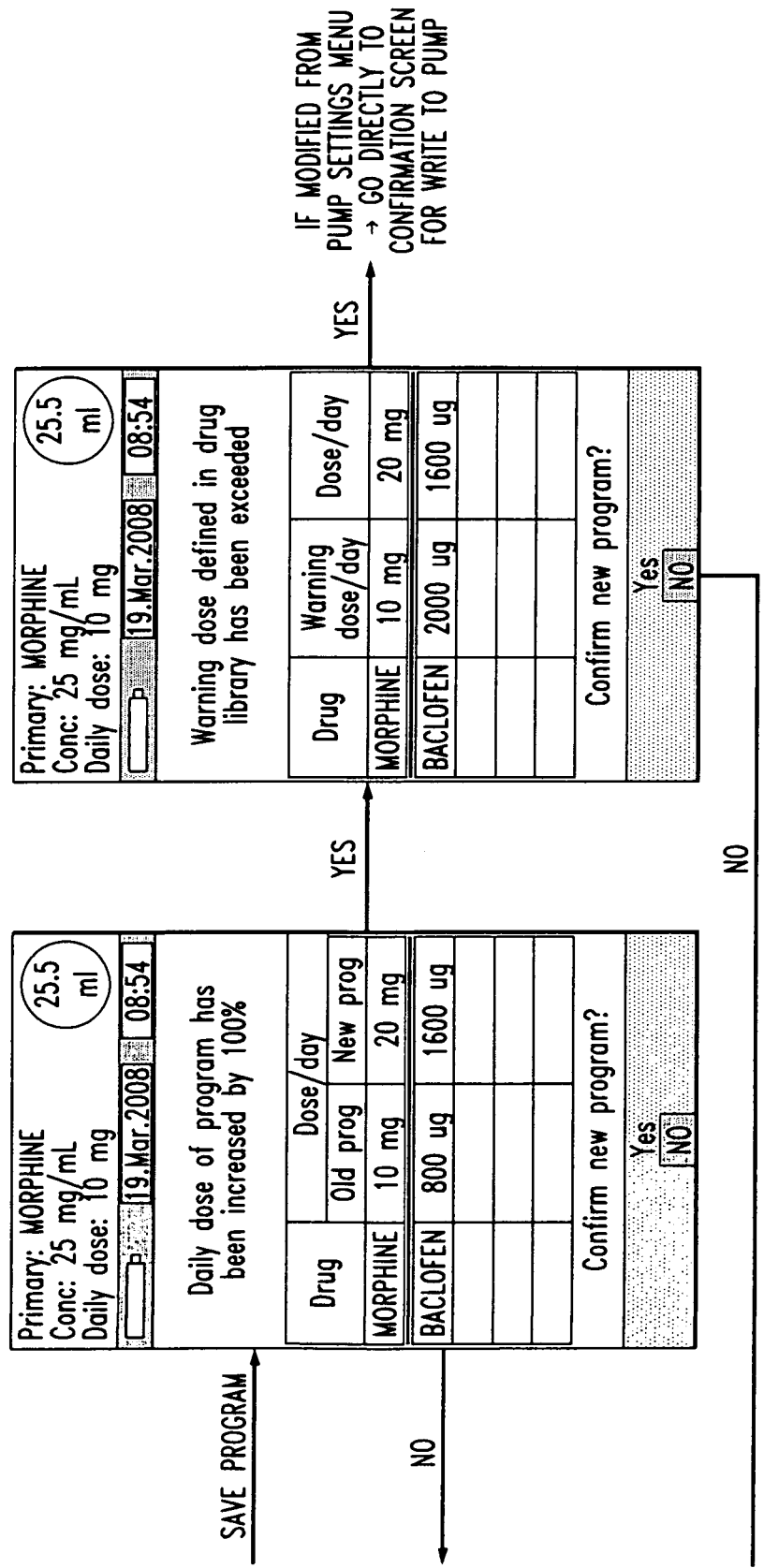

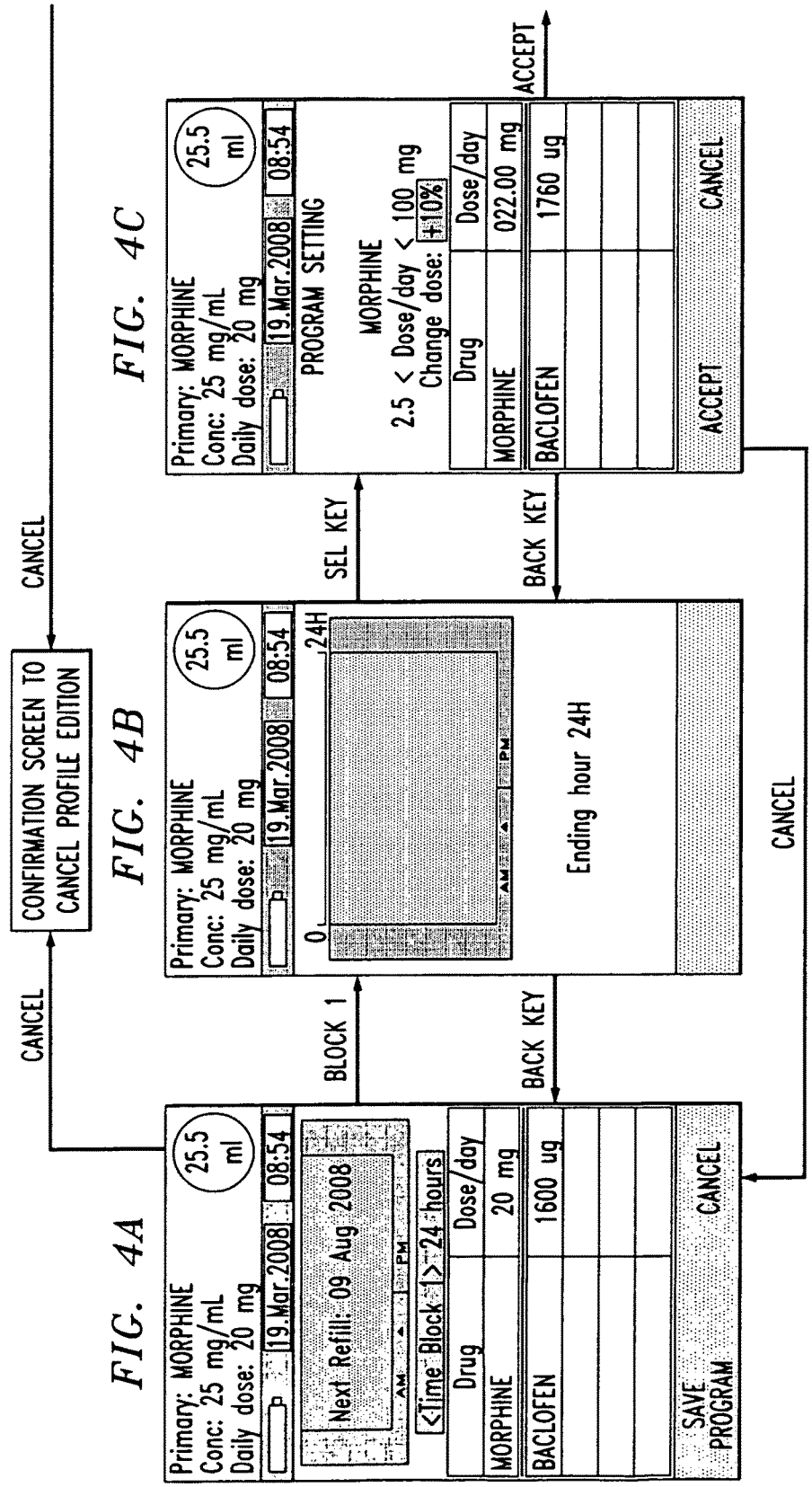

FIG. 4D

Primary: MORPHINE
Conc: 25 mg/mL
Daily dose: 20 mg
19.Mar.2008   08:54   25.5 ml Next Refill: 05 Aug 2008

<Time Block=1>=24 hours

| Drug | Dose/day | |
|---|---|---|
| MORPHINE | 22 mg | |
| BACLOFEN | 1760 ug | |

SAVE PROGRAM    CANCEL

CANCEL
ACCEPT → SAVE PROGRAM
NO

FIG. 4E

Primary: MORPHINE
Conc: 25 mg/mL
Daily dose: 20 mg
19.Mar.2008   08:54   25.5 ml Daily dose of program has been increased by 10%

| Drug | Dose/day | |
|---|---|---|
| | Old prog | New prog |
| MORPHINE | 20 mg | 22 mg |
| BACLOFEN | 1600 ug | 1760 ug |

Confirm new program?
Yes    NO

YES

FIG. 4F

Primary: MORPHINE
Conc: 25 mg/mL
Daily dose: 10 mg
19.Mar.2008   08:54   25.5 ml Warning dose defined in drug library has been exceeded

| Drug | Warning dose/day | Dose/day |
|---|---|---|
| MORPHINE | 10 mg | 22 mg |
| BACLOFEN | 2000 ug | 1760 ug |

Confirm new program?
Yes    NO

YES

IF MODIFIED FROM PUMP SETTINGS MENU → GO DIRECTLY TO CONFIRMATION SCREEN FOR WRITE TO PUMP

Primary: MORPHINE
Conc: 25 mg/mL
Daily dose: 36 mg

| 19.Mar.2008 | | 08:54 | 25.5 ml |

Next refill: 09 Aug 2008

<Time:Block 1> 0H = 8H

| Drug | Dose/Hour | Dose/day |
|------|-----------|----------|
| MORPHINE | 20 mg | 36 mg |
| BACLOFEN | 1600 ug | 2880 ug |

SAVE PROGRAM | CANCEL

FIG. 5B

Primary: MORPHINE
Conc: 25 mg/mL
Daily dose: 36 mg

| 19.Mar.2008 | | 08:54 | 25.5 ml |

0H — 8H

Ending hour 8H

CANCEL

FIG. 5C

Primary: MORPHINE
Conc: 25 mg/mL
Daily dose: 36 mg

| 19.Mar.2008 | | 08:54 | 25.5 ml |

<Time Block 1> 12AM–8AM
MORPHINE
0.1 < Dose/hour < 4.16 mg
0.8 < Block Dose < 33.28 mg
Change block dose ±10%

| Drug | Dose/hour | Block Dose |
|------|-----------|------------|
| MORPHINE | 002.75 mg | 022.00 mg |
| BACLOFEN | 220 ug | 1760 ug |

ACCEPT | CANCEL

---

Transitions:
- FIG. 5A → FIG. 5B: BLOCK 1
- FIG. 5B → FIG. 5A: BACK KEY
- FIG. 5B → FIG. 5C: SEL KEY
- FIG. 5C → FIG. 5B: BACK KEY
- ACCEPT (from 5C)
- CANCEL → CONFIRMATION SCREEN TO CANCEL PROFILE EDITION
- SCROLL UP AND FIRST BLOCK SELECTED
- SCROLL DOWN

FIG. 5D

Primary: MORPHINE
Conc: 25 mg/mL
Daily dose: 36 mg

| 19.Mar.2008 | | 08:54 | 25.5 ml |

Next Refill: 09 Aug 2008

AM / PM

<Time-Block 1> 0H — 8H

| Drug | Dose/hour | Dose/day |
|---|---|---|
| MORPHINE | 2.75 mg | 38 mg |
| BACLOFEN | 1760 ug | 3041.28 ug |
| | | |
| | | |

SAVE PROGRAM | CANCEL

↑ ACCEPT

CANCEL → CANCEL
SCROLL DOWN → SCROLL UP AND FIRST BLOCK SELECTED

FIG. 5E

Primary: MORPHINE
Conc: 25 mg/mL
Daily dose: 20 mg

| 19.Mar.2008 | | 08:54 | 25.5 ml |

Daily dose of program has been increased by 5.6%

| Drug | Dose/day | |
|---|---|---|
| | Old prog | New prog |
| MORPHINE | 36 mg | 38 mg |
| BACLOFEN | 2880 ug | 3041.28 ug |

Confirm new program?
Yes | NO

SAVE PROGRAM

NO ↓ (to 5D) / YES → (to 5F)

FIG. 5F

Primary: MORPHINE
Conc: 25 mg/mL
Daily dose: 10 mg

| 19.Mar.2008 | | 08:54 | 25.5 ml |

Warning dose defined in drug library has been exceeded

| Drug | Warning dose/day | Dose/day |
|---|---|---|
| MORPHINE | 10 mg | 20 mg |
| BACLOFEN | 2000 ug | 1600 ug |

Confirm new program?
Yes | NO

YES → IF MODIFIED FROM PUMP SETTINGS MENU → GO DIRECTLY TO CONFIRMATION SCREEN FOR WRITE TO PUMP

NO → (back to 5E)

FIG. 5G

Primary: MORPHINE
Conc: 25 mg/mL
Daily dose: 20 mg

19.Mar.2008  08:54  25.5 ml

PROGRAM SETTINGS

MORPHINE
2.5 < Dose/day < 100 mg
Change dose: +10%

| Drug | Dose/day |
|---|---|
| MORPHINE | 39.6 mg |
| BACLOFEN | 3168 ug |
|  |  |

ACCEPT · CANCEL

FIG. 5H

Primary: MORPHINE
Conc: 25 mg/mL
Daily dose: 36 mg

19.Mar.2008  08:54  25.5 ml

Next Refil: 09 Aug 2008

All Blocks ≥ 24 hours

| Drug | Dose/day |
|---|---|
| MORPHINE | 36 mg |
| BACLOFEN | 2880 ug |
|  |  |

SAVE PROGRAM · CANCEL

Transitions:
- SAVE PROGRAM →
- SELECT (5H → 5G)
- CANCEL OR BACK KEY (DISCARD CHANGES) (5G → 5H)
- ACCEPT (HIGHLIGHT SAVE PROG.) (5G → 5H)
- CANCEL →
- SCROLL UP AND FIRST BLOCK SELECTED →
- SCROLL DOWN →

FIG. 6A

SUMMARY SCREEN
Pump Size: 40 mL
Volume Left: 25.5 mL
Next Refill: 09 Aug 2008
Patient ID: WWWWWWWWWW

| Drug | Conc (/mL) | Dose/day |
|---|---|---|
| MORPHINE | XXX.XX mg | XXX.XX mg |
| BUPIVICA... | XXXX.XX ug | XXXX.XX ug |
| | | |
| | | |

Program in progress

PUMP MENU    PRINT
PROGRAM INFO

FIG. 6B

DRUG LIBRARY
→ MORPHINE
Primary drug
Daily dose:   XXX.XX mg/day
Conc:         XXX.XX mg/mL
Dose warning level: 999.99 mg/day
Conc warning level: 999.99 mg/mL
Comment:
XXXXXXXXXXXXXXXXXXXXX
XXXXXXXXXXXXXXXXXXXXX
XXXXXXXXXXXXXXXXXXXXX

PROGRAM INFO    PRINT
SUMMARY SCREEN

FIG. 6C

CONSTANT PROGRAM

Next refill: 09 Aug 2008

AM | PM

| Drug | Dose/day |
|---|---|
| MORPHINE | XXX.XX mg |
| BUPIVICANINE | XXXX.XX ug |
| | |
| | |

CATHETER INFO    PRINT
SUMMARY SCREEN

FIG. 6D

VARIABLE PROGRAM

Next refill: 09 Aug 2008

AM | PM

<TIME BLOCK 3> 6PM - 12AM

| Drug | Dose/hour | Dose/day |
|---|---|---|
| MORPHINE | XXX.XX mg | XXX.XX mg |
| BUPIVICA... | XXXX.XX ug | XXXX.XX ug |
| | | |
| | | |

CATHETER INFO    PRINT
SUMMARY SCREEN

BUPIVICAINE (NOT IN DRUG LIBRARY)

FIG. 6E

CATHETER INFO
Pump Serial Number: ABCD123456

TWO-PIECE

Intraspinal Cath: 60-2918
Original Length: 100 cm
Volume per cm: 0.00283 mL/cm
Discarded Cath Length: 25 cm
Implanted Cath Vol: 0.21225 mL Pump Cath: 60-2914
Original Length: 100 cm
Volume per cm: 0.00283 mL/cm
Discarded Cath Length: 78 cm
Implanted Cath Vol: 0.06226 mL Total Catheter Volume: 0.27451 mL

[PUMP MENU]   PRINT
SUMMARY SCREEN

BACK KEY ←
CATHETER INFO →
BACK KEY ←

FIG. 6G
MOD_DRG_SCR

19.Mar.2008  08:54

DRUG LIBRARY
[BUPIVICAINE]

Dosage unit:   mg
Dose warning level:   OFF
Conc warning level:   OFF
Comment:
Add comment

ACCEPT   CANCEL

ACCEPT: UPDATE LIST
ACCEPT

FIG. 6F

DRUG INFO
wwwwwwwwwww

Daily dose:   XXX.XX ug/day
Conc:   XXX.XX ug/mL

Not in Library

Add drug to Library

[PROGRAM INFO]   PRINT
SUMMARY SCREEN

BUPIVICAINE (NOT IN DRUG LIBRARY)

ADD DRUG TO LIBRARY →
← CANCEL

FIG. 6H
DRG_LIB_WRN_SCR

19.Mar.2008  08:54

WARNING: Refer to pump instructions for use for the list of approved drugs for MedStream.

ACCEPT   [CANCEL]

FIG. 7A

CONFIRMATION SCREEN
Pump Size: 40 mL
Volume Left: 25.5 mL
Next Refill: 09 Aug 2008
Patient ID: WWWWWWWWWW

| Drug | Conc (/mL) | Dose/day |
|---|---|---|
| MORPHINE | XXX.XX mg | XXX.XX mg |
| BUPIVICA... | XXXX.XX ug | XXXX.XX ug |
| | | |
| | | |

New program will start

[CONFIRM]
PROGRAM INFO

PROGRAM INFO + CONSTANT PROGRAM →

FIG. 7B

CONSTANT PROGRAM

Next refill: 09 Aug 2008
AM | PM

| Drug | Dose/day |
|---|---|
| MORPHINE | XXX.XX mg |
| BUPIVICAINE | XXXX.XX ug |
| | |
| | |

[CATHETER INFO]
CONFIRMATION SCREEN

PROGRAM INFO + VARIABLE PROGRAM ↓  BACK KEY OR SUMMARY SCREEN ↑

FIG. 7C

VARIABLE PROGRAM

Next refill: 09 Aug 2008
AM | PM

<TIME BLOCK 3> 6PM - 12AM

| Drug | Block Dose | Dose/day |
|---|---|---|
| MORPHINE | XXX.XX mg | XXX.XX mg |
| BUPIVICA... | XXXX.XX ug | XXXX.XX ug |
| | | |
| | | |

[CATHETER INFO]
CONFIRMATION SCREEN

CATHETER INFO → / BACK KEY ←

FIG. 7D

CATHETER INFO
Pump Serial Number: ABCD123456

TWO-PIECE

Intraspinal Cath: 60-2918
Original Length: 100 cm
Volume per cm: 0.00283 mL/cm
Discarded Cath Length: 25 cm
Implanted Cath Vol: 0.21225 mL Proximal Cath: 60-2914
Original Length: 100 cm
Volume per cm: 0.00283 mL/cm
Discarded Cath Length: 78 cm
Implanted Cath Vol: 0.06226 mL Total Catheter Volume: 0.27451 mL

[CONFIRM]
CONFIRMATION SCREEN

FIG. 8A

```
Primary: MORPHINE          ╭─────╮
Conc: 25 mg/mL             │ 25.5│
Daily dose: 36 mg          │  ml │
                           ╰─────╯
▭▭▭    19.Mar.2008    08:54
        SINGLE BOLUS
  0.03 < Bolus Dose < 999.99 mg
```

| Drug | Bolus dose | Current dose/day |
|---|---|---|
| MORPHINE | 002.00 mg | 5 mg |
| BUPIVIC... | 1 mg | 2.5 mg |
|  |  |  |
|  |  |  |

Bolus Duration 1hr 12min 0sec
Program will restart after Bolus is completed

START BOLUS    CANCEL

→ SAVE BOLUS → A CONFIRMATION SCREEN IS DISPLAYED IF THE BOLUS DOSE > 20% PROGRAM DAILY DOSE (SAME SCREEN THAN CURRENTLY)

→ CANCEL → GO BACK TO PUMP SETTINGS MENU

FIG. 8B

IMPACT ON SUMMARY SCREEN

SUMMARY SCREEN
Pump Size: 40 mL
Volume Left: 25.5 mL
Next Refill: 09 Aug 2008
Patient ID: WWWWWWWWWW

| Drug | Conc (/mL) | Dose/day |
|---|---|---|
| MORPHINE | 10 mg | 5 mg |
| BUPIVIC... | 5 mg | 2.5 mg |
|  |  |  |
|  |  |  |
|  |  |  |

Single Bolus in progress
Complete in 0 hr 36 min 0 s
Pump will be stopped
after Single Bolus is complete.

PUMP MENU        PRINT
     SINGLE BOLUS INFO

→ SINGLE BOLUS →

FIG. 8C

SINGLE BOLUS

| Drug | Prog. dose | Remaining Dose |
|---|---|---|
| MORPHINE | 2 mg | 1 mg |
| BUPIVIC... | 1 mg | 0.5 mg |
|  |  |  |
|  |  |  |
|  |  |  |

Single Bolus in progress
Complete in 0 hr 36 min 0 s
Pump will be stopped
after Single Bolus is complete.

PROGRAM INFO       PRINT
      SUMMARY SCREEN

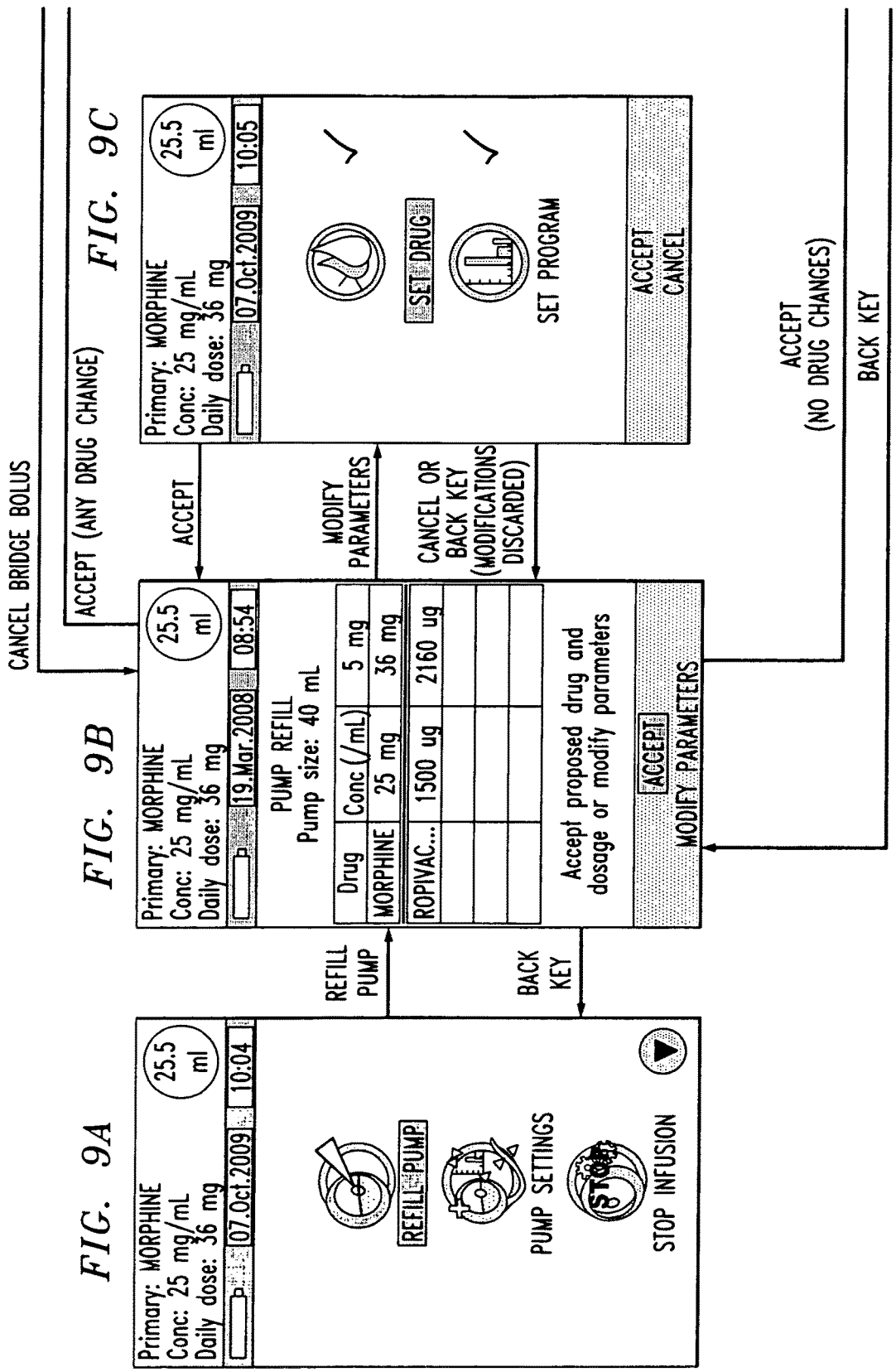

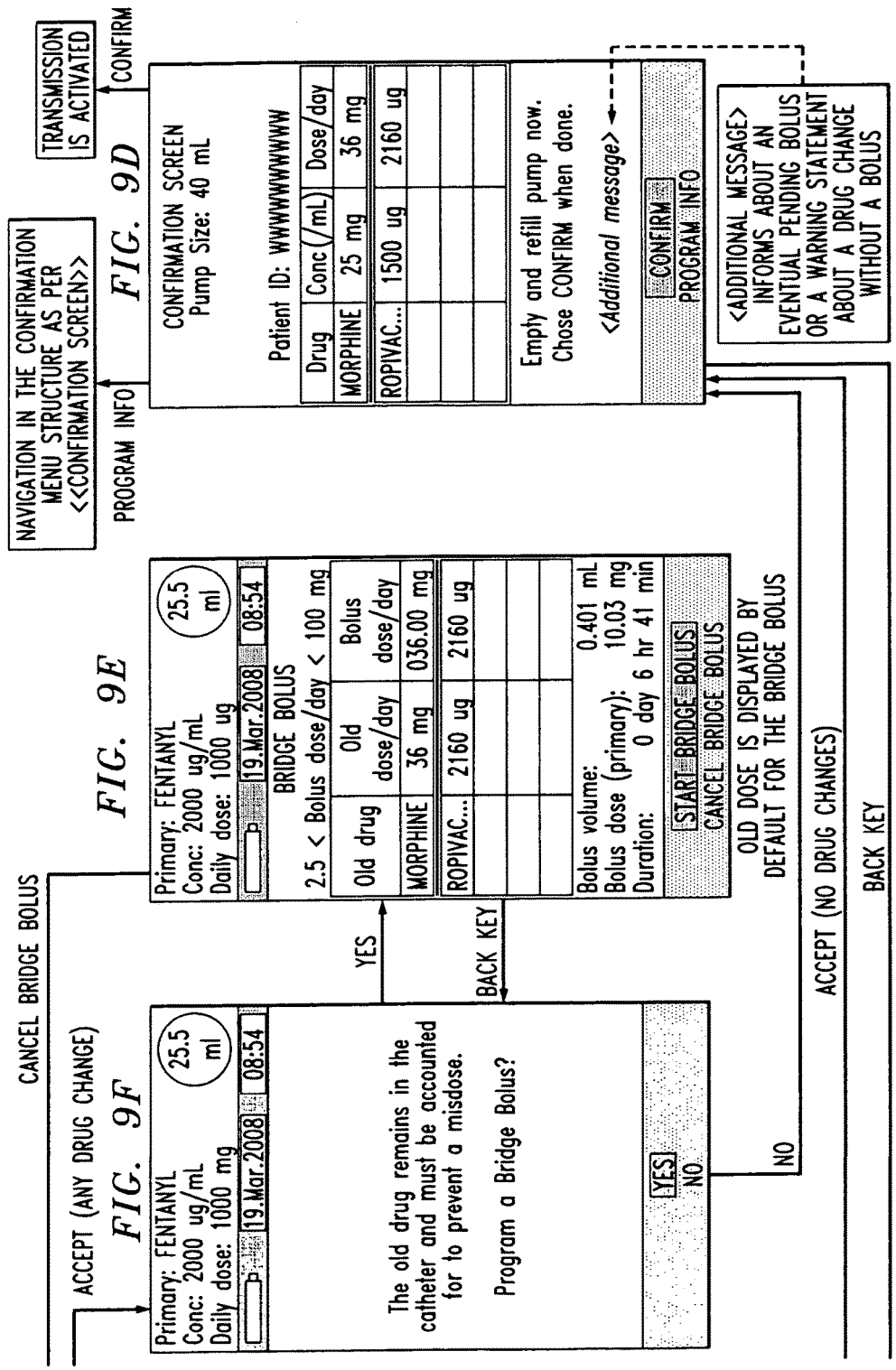

FIG. 10A

| Primary: FENTANYL |
| Conc: 2000 ug/mL |
| Daily dose: 1000 ug | 25.5 ml |

| ▭ 19.Mar.2008 ▭ 08:54 |
| BRIDGE BOLUS |
| 2.5 < Bolus dose/day < 100 mg |

| Old drug | Old dose/day | Bolus dose/day |
|---|---|---|
| MORPHINE | 36 mg | 036.00 mg |
| ROPIVAC... | 2160 ug | 2160 ug |
|  |  |  |
|  |  |  |

| Bolus volume: | 0.401 mL |
| Bolus dose (primary): | 10.03 mg |
| Duration: | 0 day 6 hr 41 min |

START BRIDGE BOLUS
CANCEL BRIDGE BOLUS

↑ SCROLL UP (3x)  
↓ SCROLL DOWN (3x)

FIG. 10B

| Primary: FENTANYL |
| Conc: 2000 ug/mL |
| Daily dose: 1000 ug | 25.5 ml |

| ▭ 19.Mar.2008 ▭ 08:54 |
| BRIDGE BOLUS |
| 2.5 < Bolus dose/day < 100 mg |

| Old drug | Old dose/day | Bolus dose/day |
|---|---|---|
| MORPHINE | 36 mg | 036.00 mg |
| ROPIVAC... | 2160 ug | 2160 ug |
|  |  |  |
|  |  |  |

| Bolus volume: | 0.401 mL |
| Bolus dose (primary): | 10.03 mg |
| Duration: | 0 day 6 hr 41 min |

START BRIDGE BOLUS
CANCEL BRIDGE BOLUS

→ SEL KEY  
← BACK KEY

FIG. 10C

| Primary: FENTANYL |
| Conc: 2000 ug/mL |
| Daily dose: 1000 ug | 25.5 ml |

| ▭ 19.Mar.2008 ▭ 08:54 |
| BRIDGE BOLUS |
| 2.5 < Bolus dose/day < 100 mg |

| Old drug | Old dose/day | Bolus dose/day |
|---|---|---|
| MORPHINE | 36 mg | 036.00 mg |
| ROPIVAC... | 2160 ug | 2160 ug |
|  |  |  |
|  |  |  |

| Bolus volume: | 0.401 mL |
| Bolus dose (primary): | 10.03 mg |
| Duration: | 0 day 6 hr 41 min |

START BRIDGE BOLUS
CANCEL BRIDGE BOLUS

↑ SCROLL DOWN (6x)  
↓ BACK KEY

FIG. 10D

| Primary: FENTANYL | | | 25.5 ml |
|---|---|---|---|
| Conc: 2000 ug/mL | | | |
| Daily dose: 1000 ug | | | |
| ▶ 19.Mar.2008 | | | 08:54 |

BRIDGE BOLUS
2.5 < Bolus dose/day < 100 mg

| Old drug | Old dose/day | Bolus dose/day | |
|---|---|---|---|
| MORPHINE | 36 mg | 030.00 mg | 2160 ug |
| ROPIVAC... | 2160 ug | | |
| | | | |
| | | | |

Bolus volume: 0.401 mL
Bolus dose (primary): 10.03 mg
Duration: 0 day 8 hr 2 min

START BRIDGE BOLUS
CANCEL BRIDGE BOLUS

SCROLL DOWN (6x) ↓

BACK KEY ↓

FIG. 10E

| Primary: FENTANYL | | | 25.5 ml |
|---|---|---|---|
| Conc: 2000 ug/mL | | | |
| Daily dose: 1000 ug | | | |
| ▶ 19.Mar.2008 | | | 08:54 |

BRIDGE BOLUS
2.5 < Bolus dose/day < 100 mg

| Old drug | Old dose/day | Bolus dose/day | |
|---|---|---|---|
| MORPHINE | 36 mg | 130.00 mg | 2160 ug |
| ROPIVAC... | 2160 ug | | |
| | | | |
| | | | |

Bolus volume: 0.401 mL
Bolus dose (primary): 10.03 mg
Duration: – day – hr – min

START BRIDGE BOLUS
CANCEL BRIDGE BOLUS

↑ IMPACT ON SUMMARY SCREEN

FIG. 10F

SUMMARY SCREEN
Pump Size: 40 mL
Volume Left: 25.5 mL
Next Refill: 09 Aug 2008
Patient ID: WWWWWWWWW

| Drug | Conc(/mL) | Dose/day |
|---|---|---|
| FENTANYL | 2000 ug | 1000 ug |
| BUPIVIC... | 1000 ug | 500 ug |
| | | |
| | | |

Bridge Bolus in progress
Remaining volume: 0.192 mL
Complete in 3 hr 12 min
Program will start after Bridge Bolus is complete.

PUMP MENU   PRINT
PROGRAM INFO

DRUG COMPONENT ADMIXTURE LIBRARY FOR A DRUG INFUSION DELIVERY SYSTEM

BACKGROUND OF THE INVENTION

Field of the Invention

The present invention relates to a drug infusion delivery system for dispensing of an admixture comprising multiple drug components. More particularly, the invention relates to a drug component admixture library for use in a drug infusion delivery system that provides intelligence and safety precautions associated with each of the individual drug components. In particular, the present inventive drug component admixture library has a safety feature that automatically generates an alert or warning when the dosage or concentration for any component of a drug admixture exceeds a maximum dosage or maximum concentration, respectively.

Description of Related Art

U.S. Pat. No. 6,269,340 discloses the concept of a drug library for use with a non-implantable syringe stored in a housing coupled to a programmer. From a standard drug library the user selects a customized drug library to be loaded into the drug infusion pump. Various parameters for the drug may be established. This drug library patented system addresses some rudimentary concerns regarding human error but fails to address more complex safety issues. For instance, the patented device fails to permit the user to define a drug admixture comprising more than one drug component from a drug library while providing intelligence and safety precautions associated with each of the individual drug components.

It is therefore desirable to develop a drug component admixture library for use with a drug infusion delivery device that provides intelligence and safety precautions associated with each of the individual drug components.

SUMMARY OF THE INVENTION

An aspect of the present invention is to provide a drug component admixture library wherein the user is able to select from the library one or more drug components comprising a drug admixture to save time and ensure a common set of names when referring to the drug components.

Another aspect of the present invention is to provide a drug component admixture library that includes intelligence and safety precautions associated with each drug component comprising the drug admixture.

Yet another aspect of the present invention is to provide a system for delivering a drug admixture wherein a dosage only need be specified for a single primary drug component, all remaining secondary drug components are automatically calculated based on the primary drug component dose specified and previously stored concentrations for each of the drug components in the admixture, thereby reducing the occurrence of human errors caused by entering inconsistent doses for different drug components that do not correspond to the drug admixture recipe or formula.

Still another aspect of the present invention relates to a method minimizing improper dosage of a drug admixture dispensed from a drug infusion delivery system, wherein the drug admixture includes a single primary drug component and at least one secondary drug component. For each drug component in the drug admixture, drug component admixture library data is received, wherein the drug component admixture library data includes a name of the drug component along with its dosage unit, a maximum dose warning level and a maximum concentration warning level. The received drug component admixture library data for each drug component in the drug admixture is stored in a first memory device. Also received from the user is: (i) a concentration for each of the single primary drug component and the at least one secondary drug component; and (ii) a dose setting of only the primary drug component. Thereafter, a calculated dose of each of the at least one secondary drug component is automatically determined using a processor based on the received dose setting for only the primary drug component and the concentration for that secondary drug component. Finally, an alert is generated when: (i) the received dose setting of the primary drug component or calculated dose setting of the at least one secondary drug component exceeds the dose warning level for that drug component stored in the first memory device; or (ii) the received concentration of the primary drug component or the at least one secondary drug component exceeds the concentration warning level for that drug component stored in the first memory device.

In addition, the present invention is also directed to a non-transitory computer readable medium having a computer readable program code embodied therein. The computer readable program code is adapted to be executed to implement a method for minimizing improper dosage of a drug admixture to be dispensed from a drug infusion delivery system, wherein the drug admixture including a single primary drug component and at least one secondary drug component. The method including the steps of: (a) providing the drug infusion delivery system, wherein the drug infusion delivery system comprises distinct software modules, and wherein the distinct software modules comprise a drug component admixture library data receiving module, a logic processing module, a drug component admixture library module and a patient prescription data transmitting/receiving module; (b) for each drug component in the drug admixture, receiving drug component admixture library data via the drug component admixture library data receiving module, wherein the drug component admixture library data includes a name for that drug component along with its dosage unit, a maximum concentration warning level and a maximum dose warning level; (c) storing in a first memory device as a drug component admixture library the received drug component admixture library data, the drug component admixture library being stored in memory using the drug component admixture library module; (d) receiving using a patient prescription data transmitting/receiving module: (i) a concentration for each of the single primary drug component and the at least one secondary drug component; and (ii) a dose setting of only the primary drug component; (e) automatically determining using the logic processing module, a calculated dose of each of the at least one secondary drug component based on the received dose setting for only the primary drug component and the received concentration for that secondary drug component; and (f) generating an alert when: (i) the received dose setting of the primary drug component or calculated dose setting of the at least one secondary drug component exceeds the dose warning level for that drug component stored in the first memory device; or (ii) the received concentration of the primary drug component or the at least one secondary drug component exceeds the concentration warning level for that drug component stored in the first memory device.

Yet still another aspect of the invention pertains to a drug infusion delivery system for minimizing improper dosage of a drug admixture to be dispensed from a drug infusion delivery system, the drug admixture including a single primary drug component and at least one secondary drug component. This system includes a control device having a data entry device, a first memory device, a processor and circuitry for generating an alert. The data entry device is used to provide: (i) for each drug component in the drug admixture, drug component admixture library data including: a name for that drug component along with its dosage unit, a maximum concentration warning level and a maximum dose warning level; (ii) a concentration for each drug component in the drug admixture and (ii) a dose setting for only the primary drug component. Stored in the first memory device for each drug component in the drug admixture is the drug component admixture library data. The functions performed by the processor include automatically determining a calculated dose of each of the at least one secondary drug component based on the received dose setting for only the primary drug component and the concentration for that secondary drug component stored in the first memory device. An alert generated by the processor is enabled when: (i) the received dose setting of the primary drug component or the calculated dose of each of the at least one secondary drug component exceeds the dose warning level for that drug component stored in the first memory device; or (ii) the concentration of the primary drug component or the at least one secondary drug component exceeds the concentration warning level for that drug component stored in the first memory device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIGS. 1A-1F depict exemplary Drug Library creation screen shots in time in accordance with the present inventive Drug Component Admixture Library;

FIGS. 2A-2J depict exemplary Set Drug screen shots in time in accordance with the present inventive Drug Component Admixture Library;

FIGS. 3A-3G depict exemplary New Dosage Program screen shots in time in accordance with the present inventive Drug Component Admixture Library;

FIGS. 4A-4F depict exemplary Modify Constant Dosage Program screen shots in time in accordance with the present inventive Drug Component Admixture Library;

FIGS. 5A-5H depict exemplary Modify Variable Dosage Program screen shots in time in accordance with the present inventive Drug Component Admixture Library;

FIGS. 6A-6H depict exemplary Summary screen shots in time in accordance with the present inventive Drug Component Admixture Library;

FIGS. 7A-7D depict exemplary Confirmation screen shots in time in accordance with the present inventive Drug Component Admixture Library;

FIGS. 8A-8C depict exemplary Single Bolus screen shots in time in accordance with the present inventive Drug Component Admixture Library;

FIGS. 9A-9F depict exemplary Pump Refill screen shots in time in accordance with the present inventive Drug Component Admixture Library;

FIGS. 10A-10F depict an exemplary Bridge Bolus screen shots in accordance with the present inventive Drug Component Admixture Library;

DETAILED DESCRIPTION OF THE INVENTION

Figure 11A:
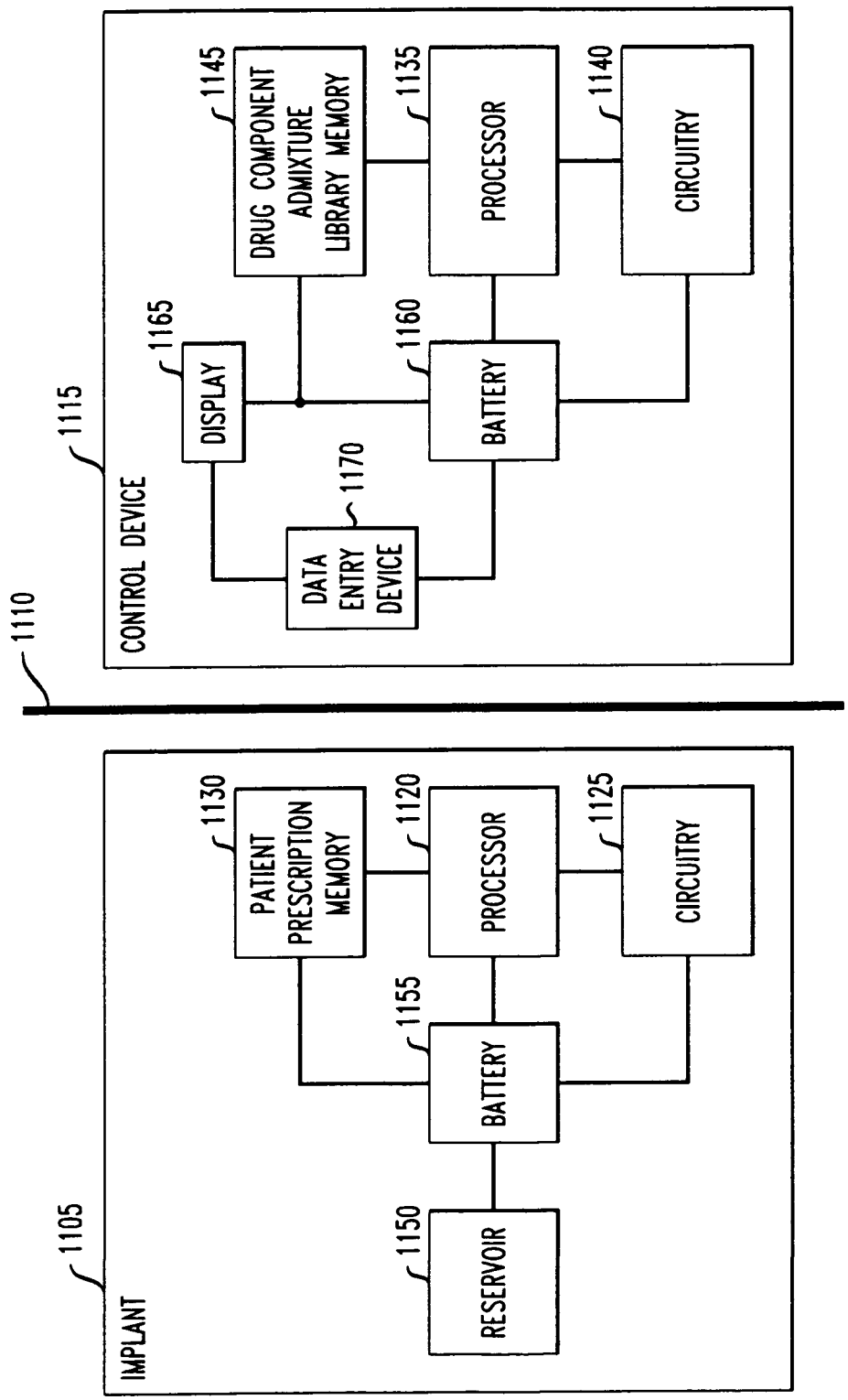
FIG. 11A shows an exemplary high level schematic diagram of a drug infusion delivery system employing the present inventive Drug Component Admixture Library.

It is not uncommon in the treatment of many disorders or illnesses to use a drug infusion delivery system for dispensing a drug into the body over a 24 hour period based on programming established by a control device. FIG. 11A shows an implantable drug infusion delivery system including an implantable device 1105 in wireless communication with an external control device 1115 through the skin 1110. A wireless interface is preferred such as RF telemetry, especially when the device 1105 is implanted in the body. Control device 1115 is powered by a battery 1160 preferably a rechargeable battery or any other type of power source. Processor or controller 1135 is used to provide such programming software including graphical user interface programming. Electrically connected to the processor 1135 is a drug component admixture library memory device 1145 for storing the drug component admixture library data and programming software. One processor and memory is illustrated in the drawings, however, it is contemplated and within the intended scope of the invention to include multiple processors and/or storage devices. Other functional electronic circuitry associated with the control device 1115 such as, but not limited to, transmitting/receiving circuitry for wireless communication, is generically represented by block 1140. A display 1165 such as a liquid crystal display (LCD) is included to generate visual screens via the graphical user interface or computer interface programming software based, on the user's programming selections received via a joystick, touch screen, keyboard or other data entry device 1170.

Figure 11B:
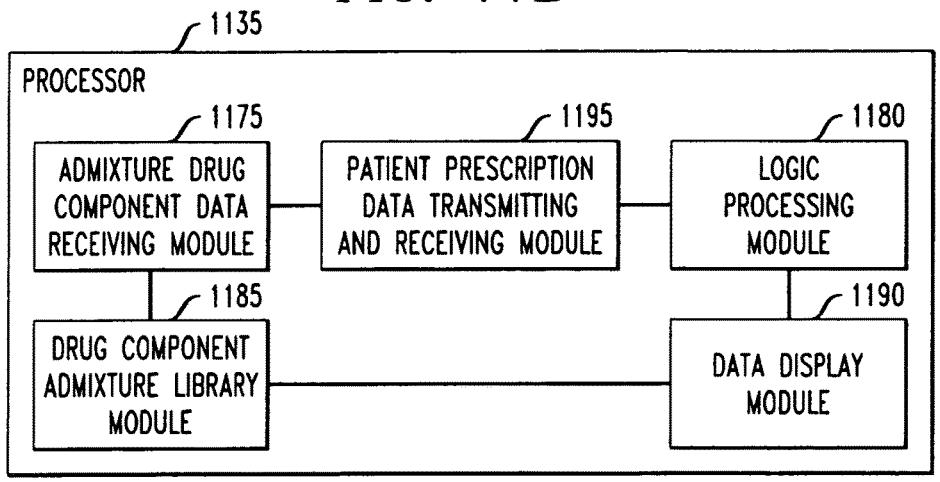
FIG. 11B shows an exemplary high level schematic diagram of the processor of the control device of FIG. 11A.

Referring to FIG. 11B, the processor 1135 of the control device 1115 includes one or more distinct software modules. By way of illustrative example, the processor 1135 depicted in FIG. 11B has an admixture drug component data receiving module 1175, a logic processing module 1180, a drug component admixture library module 1185, a data display module 1190 and a patient prescription data transmitting and receiving module 1195. Admixture drug component data receiving module 1175 receives and processes the drug component admixture library data entered by the user via the data entry device 1170. Once the data is received, the drug component admixture library module 1185 performs all processing for storing, organizing and retrieving drug component data stored in memory from the drug component admixture library. The display of drug component data along with any safety alerts/warning for any drug component in the admixture is performed by the data display module software 1190. All other processing is performed by the logic processing module 1180 including, but not limited to automatic calculations of the dose of the one or more secondary drug components in the admixture. Module 1195 receives the concentrations for each drug component in the admixture as well as the dose setting for only the primary drug component entered by the user via the data entry device 1170. Moreover, the patient prescription data transmitting and receiving module 1195 transmits the concentrations and dose settings (both the dose setting entered by the user for the primary drug component as well as the calculated dose of each of the at least one secondary drug component based on the received dose setting for only the primary drug component and the concentration for that secondary drug component, as explained in detail further below).

The system also includes an implantable drug infusion delivery device 1105 that is preferably at least partially powered by a battery 1155, either rechargeable or non-rechargeable. Power supplied by the battery 1155 is used to energize the processor 1120, patient prescription memory 1130 and circuitry generically represented by block 1125 for providing all other functionality associated with the implantable medical device. Stored in the patient prescription memory 1130 is patient specific programming data for each drug component in a drug admixture created from the drug component admixture library. The patient specific programming data stored in the patient prescription memory includes: (i) a name of each drug component; (ii) concentration of that drug component for the patient; and (iii) dose of that drug component for the patient. A drug admixture or cocktail comprising more than one drug component, part, element or ingredient is stored in a reservoir 1150 and dispensed therefrom based on specific patient prescription data established by the user via the control device 1115 and stored in the patient prescription memory 1130. FIG. 11A depicts only a single reservoir, however, more than one reservoir may be included, as desired, wherein each reservoir stores a different drug admixture.

A recipe or formula represents a ratio or percentage of each drug part, component, element or ingredient comprising the admixture stored in the reservoir 1150. For instance, a typical course of treatment today for the management of pain or spasticity is intrathecal delivery of an opiate drug admixture via the implantable drug infusion delivery device. The formula or recipe for the drug admixture may include a predetermined maximum number of drug components, or alternatively be limitless in number. By way of illustrative example, the recipe or formula for the morphine-baclofen drug admixture may be predefined as 2:1. If 2 mg dosage of Morphine is specified by the programmer then 1 mg of Baclofen will be provided in accordance with the 2:1 predefined recipe or formula. Since the drug admixture represents more than one component, certain safety conditions or precautions associated with one or more of the individual drug components may be overlooked by the physician, nurse, technician or user during programming of the drug infusion delivery device resulting in undesirable and possibly even harmful consequences to the patient. In accordance with the present invention, threshold conditions or warning levels are specified for each drug component of the admixture, as described in detail further below.

Each drug admixture includes only one primary drug component and one or more secondary drug components. A reservoir 1150 associated with the implantable drug infusion delivery device 1105 is filled with the drug admixture based on the predefined recipe or formula. As previously noted, FIG. 11A illustrates an implantable drug infusion delivery device having a single reservoir 1150 for delivery of only one drug admixture. It is, however, contemplated and within the intended scope of the present invention to expand the inventive concepts herein to apply to drug infusion delivery systems having multiple reservoirs for storing a different drug admixture in each wherein as a preliminary step the user is provided with the option of selecting from more than one drug admixture to be dispensed by the corresponding reservoir of the drug infusion delivery device.

In accordance with the present invention, each component of the drug admixture and its concentration is specified by the user (e.g., physician, nurse, technician or patient). As a time saving feature, each component of the drug admixture is selected from a Drug Component Admixture Library of previously stored information. A predetermined threshold or maximum number of specified drug components may be stored at any given time in the drug component admixture library. The drug component need only be created once and thereafter may be easily selected from a list of established drug components and their corresponding parameters retrieved from memory 1145. FIGS. 1A-1F show different screen shots of the Drug Library feature. The Drug Library is stored in drug component admixture library memory device 1145 associated with the control device 1115 information previously entered concerning one or more drug components. In the illustrated example shown in FIG. 1A representing a Main Drug Library screen, four drug components (e.g., baclofen, clonidine, morphine and saline) have been created or established in the drug library from which the user may choose in specifying the drug admixture. The user may freely scroll or navigate through the list of established drug components in the drug library by moving the cursor, roller ball, jog dial or any other recognized data entry device 1170 for selecting a particular entry from the list.

If a particular drug component of interest has not been created or established in the drug library, the last option in the list is "Add new drug." Selection of this feature enables the graphical user interface to generate, a new screen, as shown in FIG. 1B, preferably displaying a warning advising the user to review a list of approved drugs provided in the instructions for use of the drug infusion delivery device. Thereafter, affirmative acceptance by the user is awaited prior to displaying a keyboard screen (see FIG. 1C) or other means for entry by the user of the name of the new drug component to be created or added to the drug component admixture library. Display of such warning and/or affirmative acceptance by the user is desirable, but may be eliminated. Once the name of the new drug component has been specified by the user, a screen such as that shown in FIG. 1E is automatically displayed by the graphical user interface along with one or more parameter settings (e.g., dosage unit, maximum dose warning level, maximum concentration warning level, comments)(hereinafter collectively referred to as "drug component admixture library data") for the drug component. The drug component admixture library data including the name of the drug component along with its programmed dosage unit, maximum dose warning level, maximum concentration warning level and comments are stored in drug component admixture library memory device 1145. The parameter settings for the newly created drug component (Fentanyl) in FIG. 1E is by default preferably initially set to default settings. That is, in the example shown the dosage unit (e.g., mg, ug or ml), by default may be set to one particular unit. In addition, the remaining parameters (i.e., maximum dose warning level and maximum concentration warning level) are preferably turned OFF as the default setting. Dose warning level represents the maximum dose for the drug component prior to a warning or alert being generated. For example, if the maximum dose for Fentanyl is set to 10 mg/day and during programming the dose is modified to 20 mg/day, then a warning or alert will be generated. Concentration warning level represents a maximum concentration value for the drug component that if exceeded during programming will generate a warning or alert. A Comment field specifies, by default, "Add comment" awaiting the user to enter a specific comment about the new drug component being added. Such information stored in the Comment data entry field may, for example, be office specific information for the medical provider such as the name of the individual that entered the parameters, the individual to whom authorization is required to exceed the parameter settings or any other notes such as possible future dosage programs should the current dosage program prove unsuccessful. The comment field is not a required field and nothing need be specified therein.

Any default setting initially displayed for each parameter may be modified or changed by the user, as desired. After completing all of the parameter settings for the new drug component to be added to the Drug Component Admixture Library, the user selects the ACCEPT or CANCEL icon at the bottom of the screen, in FIG. 1E. In the specific case in which the name and dosage unit of the drug component being added are the same as that for an established drug component already stored in the drug library, then the ACCEPT icon will be shaded or otherwise visually indicate that it is not an available option to the user. Preferably, the ACCEPT icon will identify that the name and dosage unit of a new drug component matches that of an established drug component from the drug library regardless of whether the name is extended or padded with spaces at the beginning and/or end of the name. A confirmation screen may be automatically generated to await affirmative confirmation on the part of the user (Yes/No) prior to storing the information in the drug component admixture library memory device 1145.

If the drug component has already been created and stored in the drug component admixture library memory device 1145, it will thereafter be retrieved and displayed for selection by the user. As previously mentioned, in FIG. 1A, the drug library includes baclofen, clonidine, morphine and saline. The user may select an established drug component from the drug component admixture library. In FIG. 1D morphine has been selected by the user as an established drug component from the drug component admixture library. Since morphine has already been created its current parameters are retrieved from drug component admixture library memory device 1145 and displayed for viewing. In the example shown in FIG. 1D, the current drug component admixture library data for the drug component morphine is: (i) Dosage Unit: mg; (ii) Maximum Dose Warning Level: 010.00 mg/day; and (iii) Maximum Concentration Warning Level: 050.0 mg/ml. Any one or more of these parameters may be changed by the user selecting the MODIFY icon at the bottom of the screen. Some type of authorization (e.g., a password, ID or other form of protection) may be a precondition in order to set the maximum dose warning level or maximum concentration warning level stored in the drug component admixture library. Alternatively, the drug component may be removed in its entirety from the drug component admixture library by selecting the REMOVE icon. In either case, a confirmation screen is preferably generated by the graphical user interface confirming the intent of the user (Yes/No) prior to making such modification. If the user affirmatively confirms modifying the parameters, the drug component modification screen such as that shown in FIG. 1F is generated by the graphical user interface. Any one or more of the parameters associated with the selected drug component (e.g., morphine) may be modified, as desired. In response to a change in any one or more of the parameters the user may ACCEPT/CANCEL these changes by selecting the appropriate icon at the bottom of the screen in FIG. 1F. To avoid any unintentional errors, cancellation preferably requires an affirmative action on the part of the user in response to a confirmation screen prior to removing the drug component from the drug component admixture library memory device 1145 to avoid any unintentional errors. If the response to the confirmation is "No," then the graphical user interface automatically returns to the modify drug component screen in FIG. 1F with the current parameter settings provided as the drug component admixture library data.

It is desirable to store in the drug component admixture library a plurality of drug components and their corresponding parameter settings so that when specifying a particular formula or recipe of the admixture for a patient prescription to be held in the reservoir the user may merely select one or more drug components from the library without having to add a new drug component and its associated parameter settings. The maximum number of drug components stored in the drug component admixture library may be limited. If the number of drug components stored in the drug component admixture library is reached, thereafter, the option "Add new drug" at the bottom of the screen as shown in FIG. 1A, is preferably disabled (e.g., shaded) to denote that this feature is not available to the user. A warning or alert may be automatically displayed to explain to the user that the number of drug components stored in the library has reached its limit. It should also be mentioned that it is contemplated and within the intended scope of the present invention that the drug components stored in the drug component admixture library may include a drug that is not to be part of an admixture, but instead to be filled in the reservoir alone. Saline is such an example, wherein when selected from the drug library, no other drug component would be selected since the reservoir would be filled only with saline. The process is repeated whereby each drug component is selected from newly created and/or previously established drug components stored in the drug component admixture library until all drug components comprising the admixture have been identified by the user.

For each drug component the user sets its concentration based on a predefined recipe or formula for that drug admixture held in the reservoir 1150. In response to the user selecting a SET DRUG option from the user interface (from the screen presented in FIG. 9C), the graphical user interface software generates a summary screen listing each drug component in the drug admixture as they are identified by the user. FIG. 2A is an exemplary Set Drug Summary screen displayed wherein the drug components identified in the admixture are clonidine and baclofen. In any particular admixture comprising more than one drug component the user designates one component as a primary drug component, while by default the remaining one or more drug components in the admixture are deemed secondary drug components. Any drug component in the admixture may be identified by the user as a primary drug component. In the example shown in FIG. 2A, clonidine has been designated by the user as the primary drug component. Preferably, the primary drug component is displayed at the top of the screen. In addition, the primary drug component is preferably the first listed in the table and visually separated or distinguished from the remaining secondary drug components (e.g., baclofen) by double lines or some other visual means. Preferably, the current or default concentration for the two drug components clonidine and baclofen (10 mg/ml, and 2000 µg/ml, respectively, as shown in the screen of FIG. 2A) have been retrieved from the patient prescription memory device 1130 of the implantable drug infusion delivery device 1105 when interrogated by the control unit 1115.

An additional drug component may be added to the admixture by the user selecting the "Add drug" entry at the bottom of the list. Here again, the user is prompted with a visual warning to "Refer to instructions for use for the list of approved drugs" for the particular manufacture of the device. In response to the user enabling the "Add drug" to the admixture option, a screen such as that shown in FIG. 2B is automatically displayed by the graphical user interface. The drug components stored in the drug component admixture library are visually displayed so that the user may easily select the drug component from those already established. Once again, if the particular drug component does not exist in the drug component admixture library it may be created. For example, morphine has been selected from the drug component admixture library and identified as part of the recipe or formula for the drug admixture. After the user has specified the drug component (e.g., morphine) to comprise part of the admixture and its corresponding concentration level (e.g., 25 mg/ml), the graphical user interface automatically updates the summary screen of the drug admixture in FIG. 2C.

The concentration level of the primary drug component in the admixture may be updated or removed by merely selecting that particular drug component from the summary screen. For instance, in response to the user selecting the clonidine drug component in FIG. 2A, the Set Drug screen shown in FIG. 2D is generated by the graphical user interface. By default the parameters identified on the Set Drug screen are those currently stored in patient prescription memory device 1130. In FIG. 2D, the default parameters retrieved from the patient prescription memory device 1130 for the clonidine drug component, are its concentration level of 10 mg/ml and that it is currently designated as the primary drug. Below this parameter information the user is presented with a series of options: (i) Change Drug; (ii) Change Concentration; (iii) Remove Drug; (iv) Set as Primary Drug Component; or (v) Add Drug Component to Drug Component Admixture Library.

In response to the user selecting the Change Concentration option, a new screen is generated in FIG. 2E displaying the current concentration level which may be changed, as desired, by the user to a new concentration level. In the example being shown, the concentration level for clonidine is increased from 10 mg/ml (current concentration level) to 25 mg/ml (new concentration level). The drug component admixture library memory device 1145 includes one or more conditional thresholds which, if exceeded, would generate a warning or alert. One such conditional threshold established by the user and stored in the drug component admixture library memory 1145 is a maximum concentration warning level for each drug component. Referring once again to the example shown in FIG. 2E, by setting the new concentration level of the clonidine drug component to 25 mg, the user has exceeded the maximum concentration warning level stored in the drug admixture library and a warning is automatically displayed in red. After specifying the updated concentration level, a revised or updated summary screen is displayed for the drug component in the admixture, as shown in FIG. 2F.

Another option provided to the user in FIG. 2D is to change or substitute one drug component in the admixture for another drug component. In response to requesting such a Change Drug option, FIG. 2G is displayed wherein the selected drug component to be changed or substituted is identified at the top of the screen. Also displayed is a list of all drug components stored in the drug component admixture library memory device 1145 for easy navigation by the user simply scrolling up and down the list of entries. As with other screens previously mentioned, a New Drug option is also provided for the user to enter a substitute drug component that currently is not stored in the drug component admixture library. Morphine is selected by the user from the list of stored components in the drug component admixture library to be substituted for clonidine. A Set Drug concentration level screen such as that shown in FIG. 2E for clonidine will be displayed for morphine with the concentration. An updated or revised Summary screen is shown in FIG. 2I, wherein since morphine was selected to replace clonidine, and clonidine was designated as the primary drug component, morphine is now by default designated as the primary drug component. Of course, the user may designate a drug other than morphine as the primary drug component. The change or substitution of one drug component for another in the admixture obviously may have significant ramifications. Therefore, the system preferably displays a confirmation screen prior to updating the information stored in the drug component admixture library memory device 1145. FIG. 2J is such a confirmation screen whereby the top of the screen displays the "Old Drug" and corresponding concentration for each drug in the admixture, while the "New Drug" and corresponding concentration for each drug in the admixture is displayed at the bottom of the screen. To further emphasize this change of information the New Drug may be highlighted or displayed in a different color and/or any other visual indication to set it apart from the other, information.

Yet another option available from FIG. 2D is the Set as Primary Drug Component. In the example shown, the designated, primary drug may be changed from clonidine to baclofen. FIG. 2H shows the summary screen wherein the first drug component (primary drug component) identified is baclofen. After accepting such changes at the bottom of the screen, the information displayed at the top of the screen will identify baclofen as the new primary drug component.

Once the concentration for each drug component in the admixture has been established, the dose for the admixture must be programmed by the user and stored in patient prescription memory device 1130 along with the name of the drug component and its concentration. The user may modify an existing dosage program retrieved from the patient prescription memory device 1130 or configure a new dosage program for only the designated primary drug component in the admixture, the dosages for each of the remaining one or more secondary drug components of the admixture will be automatically calculated by the processor 1135 in the control device 1115 based on the concentration for each secondary drug component and the primary drug component dosage specified. The present invention contemplates the flexibility of providing either a constant dosage program or a variable dosage program over a predetermined period of time (e.g., 24 hr. period). Once the dose has been specified, the processor 1135 automatically calculates the flow/delivery rate based on the dose using the equation flow rate=primary drug dosage/primary drug concentration FIGS. 3A-3G show several exemplary screen shots for configuring a new dosage program for the first time. In response to selecting a NEW PROGRAM option a summary table or screen of all drug components specified in the admixture by the user is displayed. FIG. 3A is an example in which the admixture has two drug components, e.g., morphine and baclofen. Morphine is designated as the primary drug component, as is visually indicated by the fact that it is displayed at the top of the screen as well as the first entry in the summary table identifying all drug components in the admixture. Since it is a new dosage program, the default parameter daily dosage setting for each drug component in the admixture is set as 0 mg or ug. Preferably, in addition to the table identifying each drug component in the admixture with its corresponding daily dosage, the dosage constant or variable over a 24 hr. period is displayed graphically as well.

By selecting the "Add Time Block" icon the graphical user interface generates a new screen, as shown in FIG. 3B, displaying a graphical representation for the primary drug component, e.g. morphine, whereby the user sets the ending time of the $1^{st}$ block starting by default at 12 AM. In the example shown in FIG. 3B, the user has set the duration of the $1^{st}$ block starting from 12:00 AM to end at 8:00 AM. The setting of the block duration may be achieved by dragging the scroll bar at the top of the graphical representation, entering the ending time or any other means for entry of the information. In a preferred embodiment the ending time may be incremented/decremented in predetermined time interval increments (e.g., one hour intervals). Thus, if the blocks are in one hour increments, then the maximum number of blocks that may be set is 24. The graphical representation depicted in FIGS. 3B, 3D and 3E allow the user to graphically navigate between the different time frame blocks. Once the ending time for the $1^{st}$ block has been set, a summary screen of Program Settings is automatically generated by the graphical user interface such as that shown in FIG. 3C. The starting and ending time for the selected block is summarized along with the default dose/hr. and default block dose. In the table itself the parameter setting for the current dose/hr. and/or block dose of the primary drug component may be edited or changed. If the user modifies either the current dose/hr. or block dose the other parameter is automatically calculated by the processor 1135 of the control unit 1115, accordingly. Therefore, the user need only specify one parameter or the other without having to enter both. This safety feature ensures that the two parameters conform with one another. The primary drug component daily dose as well as the hourly and daily doses for each secondary drug component are automatically updated by the processor 1135 of the control unit 1115 based on the specified current dose/hr. and/or block dose of the primary drug component and concentrations for each secondary drug component in the admixture. Furthermore, the minimum and maximum dose/hr. and block dose ranges shown above the table are automatically calculated based on the specified minimum and maximum flow rates of the device.

A second time block can be set from FIG. 3E, e.g. starting from the end of the first time block at 8:00 AM and ending at 12:00 AM. The next date in which the reservoir will require refilling based on the daily dosage designed by the user is automatically calculated by the processor 1135 of the control unit 1115 and displayed on the Summary screen (see FIGS. 3D and 3E). In FIG. 3E now that the time blocks for the full 24 hour period have been specified, an icon Save Program is enabled allowing the user to save the dosage setting. As a safety precaution, the Save Program icon preferably will not be enabled unless the dosage setting has been specified for a full 24 hour period. In response to the user selecting the Save Program option, a summary change screen such as that depicted in FIG. 3F is automatically generated by the graphical user interface. Both old and new programmed dose/day are displayed side-by-side. Different colors and other visual indicators may be employed to visually set off the new settings from the old settings. A summary statement as to the percentage of increase in the dosage is provided above the table. If the changes are accurate the user takes some type of affirmative action (e.g., selecting the YES icon at the bottom of the screen) to advance to a new screen shown in FIG. 3G. In FIG. 3G, an alert is automatically enabled if an updated dosage setting for any of the drug components (i.e., the dose specified by the user for the primary drug component or the automatically calculated dosages for the secondary drug components) comprising the admixture exceeds one or more conditional thresholds specified in the drug component admixture library memory 1145 (e.g., maximum dose warning level). In the example shown in FIG. 3G, an alert is displayed indicating that the maximum dose warning level defined in the drug component admixture library has been exceeded for the primary drug component morphine. Despite exceeding the predefined maximum dose warning level the updated value may nevertheless be overridden by taking some type of affirmative action such as selecting the YES icon at the bottom of the screen. Alternatively, some type of authorization (e.g., a password, ID or other form of protection) may be a precondition in order to override the maximum dose warning level stored in the drug component admixture library.

After a new dosage program has been created for the primary drug component it may be modified, as desired. FIGS. 4A-4F show some exemplary screen shots of the modification of a constant dosage program. The current dosage program stored in memory includes a single 24 hour block summarized in FIG. 4A and graphically depicted in FIG. 4B in response to the user selecting the Time Block 1 icon in FIG. 4A. In response to the user selecting the change dosage selection icon or key, the screen shown in FIG. 4C is displayed wherein the user is able to update or revise the dose/day of the primary drug component. Since the dosage is constant throughout the day, only the dose/day parameter is displayed (the dose/hr. icon is either disabled or not displayed at all). The specific dose/day value or a percentage dose titration change either by entering a specific value or incrementing/decrementing by a predetermined interval of the primary drug component may be modified by the user. Once again, in response to the dose/day value or percentage being modified for the primary drug component, the dose/day for all remaining secondary drug components will be automatically updated or revised by processor 1135 of the control device 1115 based on the concentration stored in the patient prescription memory device 1130 for each drug component in the admixture, without requiring the user to enter the dose for each secondary drug component. It is preferred the dose/day calculations for the secondary drug components are automatically performed by the processor 1135 in real time with each digit change to the primary drug component dose/day. As previously discussed above, the maximum and minimum dose/day value range for the primary drug may be automatically determined by the processor 1135 based on the maximum and minimum flow rates available on the pump. In response to the user selecting the Accept icon in FIG. 4C, a summary screen is generated by the graphical user interface such as that shown in FIG. 4D. Since this is a constant dosage/day program there is only a single designated graphical representation block for the entire 24 hr. time frame. The user is presented with the option of saving or canceling the changes. If the information is accurate, then the Save Program icon is selected whereby the graphical user interface generates a new confirmation screen display. An example of such confirmation screen display is shown in FIG. 4E. The user is provided with a visual indication of the percentage change in daily dose. Finally, if the user confirms the accuracy of this new program another screen may be generated (see FIG. 4F) whereby the graphical user interface generates an alert or warning if any specified parameter condition (e.g., maximum dose warning level) stored in the drug component admixture library memory device 1145 is exceeded. In the example illustrated, the maximum dose warning level (10 mg) stored in the drug component admixture library memory device 1145 for the primary drug component morphine has been exceeded by the modified dose/day (22 mg).

FIGS. 5A-5H depict exemplary screen shots for modification of a variable dosage program. The currently stored dosage setting for the primary drug component throughout a 24 hour time frame is automatically retrieved from the patient prescription memory device 1130 and displayed in FIG. 5A. In this example, the current variable dosage program for the primary drug component morphine is varied between two time blocks. A first time block from 12:00 AM-8:00 AM, while a second time block begins at 8:00 AM and ends a 12:00 AM. As noted before above, the graphical representation is provided so that the user may navigate through the time blocks. In response to the user selecting the Time Block 1 icon, the graphical user interface generates an enlarged graphical representation of the time blocks in FIG. 5B. This screen allows the user to define the end time of the time block. The validation of the end time, in turn, generates a display such as that shown in FIG. 5C providing information associated with the first time block (Time Block 1) including: (i) starting time and ending time for the first time block; (ii) maximum/minimum dose/hr. for the primary drug component during this first time block; (iii) maximum/minimum block dose for the primary drug component during the first time block. As discussed above with respect to the modify constant dosage program, the user is provided with the option of either changing the specific value (e.g. dose/hr.) or a percentage change of block dose for the primary drug component during the first time block. Once again, the revised or updated dose/block of the primary drug component as well as the updated dose/block and dose/hr. for all secondary drug components will be automatically translated by the processor 1135 based on the modified dose/hr. for the primary drug component and stored concentrations for each drug component in the admixture retrieved from the patient prescription memory device 1130.

In response to the user selecting the Accept icon at the bottom of the screen in FIG. 5C, the graphical user interface generates a summary screen with the modifications, as shown in FIG. 5D. The screen includes both a graphical representation of the different time blocks over the 24 hour time frame from which the user may navigate between as well as a table of specific dosage parameter values for each component in the drug admixture. If the information entered is correct, in response to the user selecting the Save Program icon, a new screen (FIG. 5E) is generated in which the percentage modification in the variable dosage program is visualized so that the user may readily recognize any errors. Assuming that all information modified is correct, the user will confirm that the program changes are accurate, whereby the graphical user interface may generate a final screen alerting or warning the user concerning any conditional parameter thresholds (e.g., maximum dose warning level) for any of the drug components of the admixture that have been exceeded due to the modification in variable dosage program. In the example represented in FIG. 5F, the modified daily dosage (20 mg/ml) for the primary drug component morphine exceeds that of the stored maximum Dose Warning Level (10 mg/ml) for morphine stored in the drug component admixture library memory 1145. This alert or warning may nevertheless be ignored in response to the user confirming acceptance of the modified dosage parameters.

From the screen FIG. 5A, the user is free to scroll between the specified drug components in the different time blocks to modify the dose/day for a particular drug component. In the example illustrated in FIG. 5H, the user has selected the option of selecting all blocks (24 hours) thereby setting a daily dose. A current dose/day of 36 mg is increased by 10% to 36.9 mg, as depicted in FIG. 5I. Changes to the dose/day may be accepted or canceled by selecting the appropriate icon at the bottom of the screen.

As previously noted, the implantable drug infusion delivery device 1105 has an internal or associated patient prescription memory device 1130 for storage of the admixture recipe, in particular, the name of each drug component comprising the admixture along with its corresponding programmed concentration and dose. In response to the control device 1115 interrogating the drug infusion delivery device 1105, the information is retrieved from the patient prescription memory device 1130 and transmitted to the control device 1115 to be displayed on the control device using the graphical user interface. FIG. 6A is an exemplary screen shot of a drug admixture retrieved from the patient prescription memory device 1130 of the drug infusion delivery device 1105 comprising two drug components (morphine and bupivicaine). The name of the drug component may be truncated if it exceeds a predetermined maximum number of characters, as is the case for bupiviciane in FIG. 6A. In this example, morphine is a stored drug library component, whereas the drug component bupivicaine is not. Since morphine is a stored component in the drug library, the current parameter settings for this drug component may be retrieved from the drug component admixture library memory device 1145. An example screen shot of the drug information for the drug component morphine retrieved from the drug component admixture library memory device 1145 is shown in FIG. 6B. Along with the name of the drug, if applicable, the designation of the drug component as being a primary drug component is provided. Additional information included is the dose unit; maximum dose, warning level; maximum concentration warning level; and a Comment is retrieved from the drug component admixture library memory device 1145.

The summary screen identifies the pump size, volume of admixture remaining in the reservoir, the anticipated or calculated next day for refill of the reservoir with the admixture, and a unique Patient ID. For each drug component in the admixture, its name, concentration and dose/day is provided. By selecting the Program Info icon at the bottom of the screen the user is provided with the option of displaying the dosage program (which may be either a constant dosage program or a variable dosage program). An exemplary constant dosage program summary screen is shown in FIG. 6C, whereas an exemplary variable dosage program summary screen is shown in FIG. 6D. In both the constant and variable dosage program summary screens a graphical representation is provided of the one or more time blocks over the 24 hour time frame as well as a table listing each drug component in the admixture along with its current dose/day and/or dose/hour (if the program is a variable dosage). As in the past, here again the user may easily navigate through the graphical representation blocks to make a particular time block selection.

From either the constant or variable dosage program summary screens the user can select the Catheter Info icon to generate a new screen such as that shown in FIG. 6E. The information provided on this catheter information summary screen preferably includes: (i) pump serial number and (ii) number of pieces (e.g., two piece). Additional information may be specified for each piece of the pump such as: (i) catheter model number; (ii) original length; (iii) volume per cm; (iv) discarded catheter length; and (v) implanted catheter volume. In the example shown in FIG. 6E, the catheter is a two piece catheter comprising an intraspinal catheter and a pump catheter. The total catheter volume of the two pieces is specified at the bottom of the screen. A catheter comprising any number of one or more pieces may be employed.

If a particular drug component is not stored in the drug component admixture library memory device 1145, for example, the drug component bupivicaine in FIG. 6A, then a drug information screen is generated for that drug component such as that shown in FIG. 6F. The drug information screen identifies the drug by name as well as providing its daily dose and concentration. An acknowledging statement is displayed as a reminder to the user that the drug component is not in the library, below which statement the user is presented with the option of adding the drug component to the drug component admixture library. Preferably, a warning or alert screen is then generated prompting the user to refer to the device instructions for the list of approved drugs to be used. In response to receiving the user's affirmative acknowledgment of such action, an entry is created for the new drug component assigned the name bupivicaine and the parameters for that drug are either maintained at their default settings or modified by the user. Such information when accepted by the user is stored in the drug component admixture library memory device 1145.

Prior to transmitting updated or new information concerning the drug component admixture to the implanted drug infusion delivery device, the control unit generates a confirmation screen so that the information may be reviewed for accuracy one last time by the user and any errors corrected. FIGS. 7A-7D show a series of exemplary screen shots for the confirmation option. A confirmation screen is shown in FIG. 7A. The information provided in this confirmation screen preferably is the same as that provided in the summary screens discussed above (for example, in FIG. 6A). Similar to that discussed above with respect to FIGS. 6C and 6D the user has the option of visualizing the details of the constant or variable drug dosage program. Other information viewable by the user is that relating to the catheter as shown in FIG. 7D (a description of which was previously provided with respect to FIG. 6E). This description concerning FIGS. 7A-7D are associated with a confirmation screen prior to transmitting new or updated information concerning the drug admixture to the drug infusion delivery device. A confirmation screen is also preferably employed at the end of all processes modifying the parameters or status of the drug infusion delivery device (e.g., the process for refilling the reservoir with the admixture). The confirmation screen identifies the pump size, volume of drug admixture remaining, date of next refill, Patient ID and each component of the drug admixture with its corresponding concentration and daily dosage. Dose and concentration data will not be transmitted to the implant from the control unit nor will the admixture be dispensed according to the current dosage program until the user has selected the Confirm icon.

The user is also provided the option of selecting a SINGLE BOLUS. In response to such a selection, the graphical user interface generates a Single. Bolus screen such as that shown in FIG. 8A. Information displayed on the Single Bolus summary screen includes an identification of the designated primary drug component. By way of example, FIG. 8A is a Single Bolus screen shot for an admixture comprising morphine as the primary drug component and bupivicaine as a secondary drug component. The bolus dose of only the primary drug component, morphine, may be modified as desired within the specified maximum and minimum bolus dose range. In response to the user selecting the Start Bolus icon at the bottom of the screen, if the bolus dose is greater than a predetermined percentage (e.g., 20%) of the programmed daily dose then a warning or alert is displayed.

During the dispensing of the single bolus, the summary screen will be updated to include a visual indication designating that the bolus is currently in progress, as shown in FIG. 8B. Additional information displayed preferably includes the time remaining until completion of the single bolus. The display of information may be restricted or limited to include only single bolus information in response to the user selecting the Single Bolus Info icon at the bottom of the screen in FIG. 8B. An exemplary single bolus information screen is shown in FIG. 8C.

A Pump Refill Summary screen as shown in FIG. 9B is generated by the graphical user interface programming when the user selects the Refill Pump Icon in FIG. 9A. The Pump Refill screen indicates the pump size/capacity, as well as a table of all drug components and their concentration and dose/day for all drug components in the current admixture. Also indicated is the drug component designated as the primary drug component (e.g., the component above the double lines in the table). Drug admixture parameters can be adjusted by selecting the Modify Parameters option at the bottom of the screen. In response thereto, the graphical user interface generates the screen shown in FIG. 9C with two functional icons, i.e., Set Drug and Set Program. The Set Drug icon when selected generates a screen such as that shown in FIG. 2A. Selection of the Set Program icon generates a New Program (FIG. 3A) or Modify Constant Program (FIG. 4A)/Modify Variable Program (FIG. 5A) screen, depending on whether the drug component information is being entered for the first time or changed. The ACCEPT icon at the bottom of the screen is not highlighted to be selected until both drug and program are specified. A change of the drug will automatically reset the program.

When both the Set Drug and Set Program have been completed, in response to the user selecting the ACCEPT icon, the graphical user interface generates a new screen illustrated in FIG. 9F displaying the message that "The old drug remains in the catheter and must be accounted for to prevent a misdose." In the example depicted in FIG. 9F, the primary drug component has been changed from morphine at a concentration of 25 mg/ml and daily dose of 36 mg to fentanyl at a concentration of 2000 ug/ml and daily dose of 1000 ug. To initiate the Bridge Bolus programming, the user selects the "Yes" icon at the bottom of the screen. A summary Bridge Bolus screen such as that shown in FIG. 9E visually displays both the old daily dose and bolus dose for each drug component. As previously noted with respect to other functions discussed above, a confirmation screen may be generated prior to updating the information.

However, if no adjustments are made to the drug admixture parameters, in response to the user selecting the ACCEPT icon at the bottom of FIG. 9B, the graphical user interface generates a confirmation screen as shown in FIG.

9D displaying instructions for the user to empty and refill the pump as well as confirm when such action has been completed.

At the end of a refill process the user may select the BRIDGE BOLUS option in FIG. 9F, in response to which the graphical user interface generates a Bridge Bolus screen such as that shown in FIG. 10A. The bridge bolus manages the transition between the old drug remaining in the catheter and pump fluidic pathway and the new drug refilled in the reservoir. The Bridge Bolus screen displays a table indicating for each drug component the daily dosage previously delivered for the old drug and a proposed bridge bolus dose/day. The user has the option to change the bridge bolus dose/day as depicted by the examples shown in FIGS. 10B-10E. If the specified bridge bolus dose/day exceeds the technically possible or specified range specified then a warning or alert will be activated. For example, as shown in FIG. 10E, the proposed bridge bolus dose/day is 130.00 mg, outside the maximum technically possible or specified bridge bolus dose/day of 100 mg. Additional features may be enabled if such proposed value is not within acceptable mix/max limits such as, but not limited to, the following: (i) highlighting of the min/max value in a color; (ii) a symbol such as "-" is substituted for the previously entered duration parameter; and/or (iii) the START BRIDGE BOLUS option is grayed or otherwise indicated as not being available. While the Bridge Bolus is being dispensed, a Summary Screen such as that shown in FIG. 10F is generated indicating that the Bridge Bolus is in progress, while specifying the flow rate and the time of completion of the Bridge Bolus processing before returning to the dosage program.

Any user friendly means may be utilized to navigate between screens such as, but in no way limited to, selection of a back key to return to a previous screen. Furthermore, the user may scroll down (forward) and up (backwards) through the different option screens using the roller key or up/down cursor keys. Colors or any other visual means may be used in the screens to differentiate: (i) fields that may be edited; (ii) options available or enabled for selection by the user; (iii) fields in editing mode; (iv) critical changed values; (v) options disabled. Furthermore, any warning or alert may be visual, audible and/or tactile.

Figure 12:
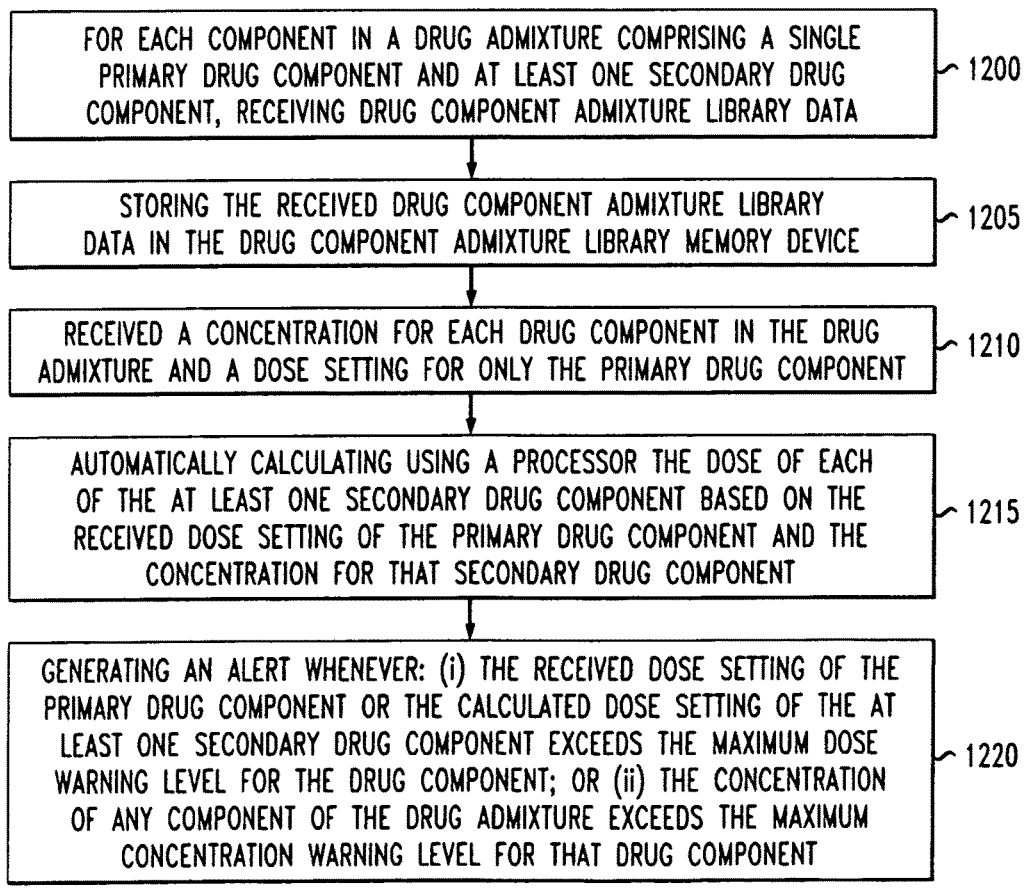
FIG. 12 shows an exemplary high level flow chart of the process for using the present inventive Drug Component Admixture Library in a drug infusion delivery system.

FIG. 12 is an exemplary flow chart of the steps performed in utilizing a drug component admixture library in accordance with the present invention to program the flow rate of drug being dispensed from a drug infusion delivery device. Initially, in step 1200 for each component in a drug admixture comprising a single primary drug component and at least one secondary drug component, receiving drug component admixture library data including: a name of the drug component along with its dosage unit, a maximum dose warning level and a maximum concentration warning level. A comment field may also be included in the drug component admixture library data, but is not required. The first time drug component admixture library data for a particular drug component is received from the user it is stored in the drug component admixture library memory device 1145, in step 1205. Thereafter the drug component admixture library data is retrieved from the drug component admixture library memory device 1145 without having to be reentered by the user. In step 1210, receiving from the user patient prescription data including: (i) a concentration for each drug component in the drug admixture (e.g., the single primary drug component and the at least one secondary drug component); and (ii) a dose setting of only the single primary drug component. The processor 1135 automatically calculates the dose of each of the at least one secondary drug component in the admixture based on the received dose setting of the primary drug component and the concentration for that secondary drug component stored in the patient prescription memory device, in step 1215. Lastly, in step 1220, an alert/warning is generated whenever: (i) the received dose setting of the primary drug component or calculated dose setting of the at least one secondary drug component exceeds the dose warning level stored in the drug component admixture library memory device for that drug component; or (ii) the received concentration of the single primary drug component or the at least one secondary drug component exceeds the concentration warning level for that drug component stored in the drug admixture library. The patient prescription data including the received concentration for each drug component in the drug admixture, the received dose setting of only the primary drug component and the calculated dose of each of the at least one secondary drug components are transmitted from the control unit to the implant and stored in the patient prescription memory device.

When configuring a drug admixture, the user can select from those drug components already stored in the drug component admixture library or add a new drug component to the library. This is not only a time saving aspect of the invention but also helps to ensure that the physicians use the same names when referring to the drug components. Furthermore, the safety parameter conditions or thresholds (maximum dose warning level and/or maximum concentration warning level) substantially mitigate safety errors. That is the user may be prevented or at the very least alerted to the fact that a specified concentration and/or dose for a particular drug component exceeds a maximum threshold stored in the drug component admixture library memory device 1145. Since only the primary drug component dose need be specified, while the secondary drug components are automatically calculated based on the primary drug component dose specified and the concentrations stored in the patient prescription memory device 1130, human errors caused by entering inconsistent doses for different drug components that do not correspond to the drug admixture recipe or formula are reduced. An additional safety feature is the maximum dose warning level and the maximum concentration warning level specified for each component in the drug admixture that triggers a warning/alert whenever the dose, or concentration of any one of the components is exceeded.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for minimizing improper dosage of a drug admixture dispensed from a reservoir of a drug infusion delivery system, the drug admixture including a single primary drug component and at least one secondary drug component, comprising the steps of:

for each drug component in the drug admixture, receiving as user input from a surface of a data entry device drug component admixture library data including a name of the drug component along with its dosage unit, a maximum dose warning level and a maximum concentration warning level; storing in a first memory device the received drug component admixture library data for each drug component in the drug admixture;

receiving as additional user input (i) a concentration for each of the single primary drug component and the at least one secondary drug component; and (ii) a dose setting of only the primary drug component;

automatically determining using a processor, a calculated dose of each of the at least one secondary drug component based on the received dose setting for only the primary drug component and the concentration for that secondary drug component;

generating an alert when: (i) the received dose setting of the primary drug component or calculated dose setting of the at least one secondary drug component exceeds the dose warning level for that drug component stored in the first memory device; or (ii) the received concentration of the primary drug component or the at least one secondary drug component exceeds the concentration warning level for that drug component stored in the first memory device;

if no alert is generated, dispensing the drug admixture from the reservoir of the drug infusion delivery system.

2. The method in accordance with claim 1, wherein the received dose setting for only the primary drug component is a new dose setting or a modified dose setting from that of a previous dose setting for only the primary drug component.

3. The method in accordance with claim 2, wherein the received dose setting for only the primary drug component is the modified dose setting of the primary drug component expressed as a percentage increase/decrease based on the previous dose setting.

4. The method in accordance with claim 3, further comprising the step of displaying the percentage increase/decrease in the dose setting of the primary drug component.

5. The method in accordance with claim 1, wherein the automatic determining step further comprises the step of automatically updating a daily dose of the primary drug component based on a received hourly dose and/or time period block dose of the primary drug component.

6. The method in accordance with claim 5, wherein the automatic determining step further comprises the step of automatically updating hourly and/or daily doses for each of the at least one secondary drug components based on the received concentration of that secondary drug component.

7. The method in accordance with claim 1, wherein the drug infusion delivery system includes an implantable drug infusion delivery device and the external control device, the processor and the first memory device are associated with the external control device, a second memory device associated with the implantable drug infusion delivery device stores patient prescription data including: (i) the received concentration for each of the primary drug component and the at least one secondary drug component; (ii) the received dose setting of only the primary drug component; and (iii) the calculated dose of each of the at least one secondary drug component.

8. The method in accordance with claim 7, further comprising the step of transmitting new and/or updated patient prescription data from the control device to the implantable drug infusion delivery device.

9. A non-transitory computer readable medium having a computer readable program code embodied therein, the computer readable program code adapted to be executed to implement a method for minimizing improper dosage of a drug admixture to be dispensed from a reservoir of a drug infusion delivery system, the drug admixture including a single primary drug component and at least one secondary drug component, the method comprising the steps of:

providing the drug infusion delivery system, wherein the drug infusion delivery system comprises distinct software modules, and wherein the distinct software modules comprise a drug component admixture library data receiving module, a logic processing module, a drug component admixture library module and a patient prescription data transmitting/receiving module;

for each drug component in the drug admixture, receiving as user input from a surface of a data entry device drug component admixture library data via the drug component admixture library data receiving module, wherein the drug component admixture library data includes a name for that drug component along with its dosage unit, a maximum concentration warning level and a maximum dose warning level;

storing in a first memory device as a drug component admixture library the received drug component admixture library data, the drug component admixture library being stored in memory using the drug component admixture library module;

receiving as additional user input using a patient prescription data transmitting/receiving module: (i) a concentration for each of the single primary drug component and the at least one secondary drug component; and (ii) a dose setting of only the primary drug component;

automatically determining using the logic processing module, a calculated dose of each of the at least one secondary drug component based on the received dose setting for only the primary drug component and the received concentration for that secondary drug component; and generating an alert when: (i) the received dose setting of the primary drug component or calculated dose setting of the at least one secondary drug component exceeds the dose warning level for that drug component stored in the first memory device; or (ii) the received concentration of the primary drug component or the at least one secondary drug component exceeds the concentration warning level for that drug component stored in the first memory device;

if no alert is generated, dispensing the drug admixture from the reservoir of the drug infusion delivery system.

10. The non-transitory computer readable medium in accordance with claim 9, wherein the dose setting for only the received primary drug component is a new dose setting or a modified dose to a previous dose setting for only the primary drug component.

11. The non-transitory computer readable medium in accordance with claim 10, wherein the received dose setting for only the primary drug component received is the modified dose of a previous dose setting of the primary drug component expressed as a percentage increase/decrease based on the previous dose setting.

12. The non-transitory computer readable medium in accordance with claim 11, wherein the drug infusion delivery system includes a data display module, further comprising the step of displaying using the data display module the percentage increase/decrease in the dose setting of the primary drug component.

13. The non-transitory computer readable medium in accordance with claim 9, wherein the automatic determining step further comprises the step of automatically updating a daily dose of the primary drug component based on a received hourly dose and/or time period block dose of the primary drug component.

14. The non-transitory computer readable medium in accordance with claim 13, wherein the automatic determining step further comprises the step of automatically updating hourly and/or daily doses for each of the at least one secondary drug components based on the received concentration of that secondary drug component.

15. The non-transitory computer readable medium in accordance with claim 9, wherein the drug infusion delivery system includes an implantable drug infusion delivery device and an external control device, the distinct software modules and the first memory device being associated with the external control device; a second memory device associated with the implantable drug infusion delivery device stores patient prescription data including: (i) the received concentration for each of the primary drug component and the at least one secondary drug component; (ii) the received dose setting of only the primary drug component; and (iii) the calculated dose of each of the at least one secondary drug component.

16. The non-transitory computer readable medium in accordance with claim 9, further comprising the step of transmitting new and/or updated patient prescription data received by the control device to the implantable drug infusion delivery device via the patient prescription data transmitting/receiving module to be stored in a second memory device associated with the implantable drug infusion delivery device.

17. A drug infusion delivery system for minimizing improper dosage of a drug admixture to be dispensed from a reservoir of a drug infusion delivery system, the drug admixture including a single primary drug component and at least one secondary drug component, the system comprising:
    a control device comprising:
        a data entry device for providing: (i) for each drug component in the drug admixture, drug component admixture library data received as user input from a surface of a data entry device including: a name for that drug component along with its dosage unit, a maximum concentration warning level and a maximum dose warning level; (ii) a concentration for each drug component in the drug admixture and (ii) a dose setting for only the primary drug component;
        a first memory device for storing for each drug component in the drug admixture the drug component admixture library data; and
        a processor for automatically determining a calculated dose of each of the at least one secondary drug component based on the received dose setting for only the primary drug component and the concentration for that secondary drug component stored in the first memory device; and
        circuitry for generating an alert initiated by the processor when: (i) the received dose setting of the primary drug component or the calculated dose of each of the at least one secondary drug component exceeds the dose warning level for that drug component stored in the first memory device; or (ii) the concentration of the primary drug component or the at least one secondary drug component exceeds the concentration warning level for that drug component stored in the first memory device; if no alert is generated, the circuitry dispensing the drug admixture from the reservoir of the drug infusion delivery system.

18. The drug infusion delivery system in accordance with claim 17, wherein the dose setting for only the primary drug component is a new dose setting or a modified dose to a previous dose setting for only the single primary drug component.

19. The drug infusion delivery system in accordance with claim 18, wherein the dose setting for only the primary drug component is the modified dose of the previous dose setting of the primary drug component expressed as a percentage increase/decrease based on the previous dose setting.

20. The drug infusion delivery system in accordance with claim 19, wherein the control device further comprises a display for displaying the percentage increase/decrease in the dose setting of the primary drug component.

21. The drug infusion delivery system in accordance with claim 17, wherein the processor performs the further function of automatically updating a daily dose of the primary drug component based on a specified hourly dose and/or time period block dose of the primary drug component.

22. The drug infusion delivery system in accordance with claim 21, wherein the automatic determining function performed by the processor further comprises the step of automatically updating hourly and/or daily doses for each of the at least one secondary drug components based on the concentration of that secondary drug component stored in a second memory.

23. The drug infusion delivery system in accordance with claim 17, further comprising an implantable drug infusion delivery device; new and/or updated concentration and dose data being transmitted from the control device to the implantable drug infusion delivery device and stored in a second memory device associated with the implantable drug infusion delivery device.

* * * * *